United States Patent [19]
Fukuda et al.

[11] Patent Number: 5,786,486
[45] Date of Patent: Jul. 28, 1998

[54] ACRYLAMIDE DERIVATIVES AND PROCESS FOR PRODUCTION THEREOF

[75] Inventors: Yasumichi Fukuda; Shigeki Seto; Yasuo Oomori; Hiroyuki Ebisu, all of Tochigi; Shiro Terashima, Tokyo, all of Japan

[73] Assignees: Kyorin Pharmaceutical Co., Ltd., Tokyo; Sagami Chemical Research Center, Kanagawa, both of Japan

[21] Appl. No.: 849,160

[22] PCT Filed: Nov. 28, 1995

[86] PCT No.: PCT/JP95/02413

§ 371 Date: May 13, 1997

§ 102(e) Date: May 13, 1997

[87] PCT Pub. No.: WO96/16965

PCT Pub. Date: Jun. 6, 1996

[30] Foreign Application Priority Data

Nov. 29, 1994 [JP] Japan .................. 6-295274

[51] Int. Cl.$^6$ .............. C07D 487/00; C07D 487/02; C07D 209/04; C07C 13/465
[52] U.S. Cl. .................. 548/421; 548/433; 548/491; 585/427
[58] Field of Search .................. 548/491, 433, 548/421; 585/27

[56] References Cited

FOREIGN PATENT DOCUMENTS

| | | |
|---|---|---|
| 0520435 | 12/1992 | European Pat. Off. . |
| 60-193989 | 10/1985 | Japan . |
| 2-502005 | 7/1990 | Japan . |
| 9404535 | 3/1994 | WIPO . |

*Primary Examiner*—Johann Richter
*Assistant Examiner*—Dominic Keating
*Attorney, Agent, or Firm*—McAulay Fisher Nissen Goldberg & Kiel, LLP

[57] ABSTRACT

Acrylamide derivatives represented by General Formula (1) below:

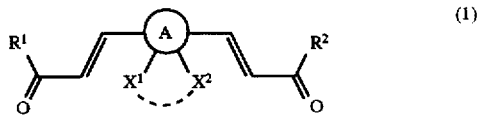

(1)

(One specific example of General Formula (1) is methyl (S,S)-3,3'-[3,3'-(1,4-phenylenediacryloyl)]-bis[1-chloromethyl-5-hydroxy-7-triflouromethyl-1, 2,3,6-tetrahydropyrrolo[3,2-e]indole-8-carboxylate.)

The acrylamide derivatives represented by General Formula (1) is highly selective to cancer cells, less toxic, and highly active also against solid tumor.

28 Claims, No Drawings

ACRYLAMIDE DERIVATIVES AND PROCESS FOR PRODUCTION THEREOF

This application is A 371 PCT/JP95/02413 filed Nov. 28, 1995.

TECHNICAL FIELD

The present invention relates to novel acrylamide derivatives, and optically active isomers and pharmaceutically acceptable salts thereof, which have antimicrobial and antitumor activities.

BACKGROUND TECHNIQUES

CC-1065, which has antimicrobial and antitumor activities, is disclosed in J. Antibiotics.: Vol. 31, p. 1211 (1978), and Vol. 34, p. 1119 (1981); and U.S. Pat. No. 4,169,888. Duocarmycin A having a similar structure, and analogues thereof are disclosed in WO87/06265, EP0318056, and J. Antibiotics: Vol. 42, p. 1229 (1989), and JP-A-4-99774.

Derivatives of CC-1065 are disclosed in EP0359454, JP-A-60-193989; and Japanese Kohyo 2-502005. Derivatives of duocarmycins are disclosed in JP-A-3-7287, JP-A-3-128379, EP0354583, and EP0406749. All of these substances have a basic skeleton of natural substances, or derived by chemical odification of natural substances.

Compounds having two tetrahydropyrroloindole skeletons in the molecule are included in the claims of JP-A-60-193989 (EP0154445) and Japanese Kohyo-2-502005 (WO8804659). However, no specific compounds is mentioned, and no example is disclosed about the corresponding compounds. Compounds having a -R$_5$-T-R'$_5$- group as a bridging moiety (where R$_5$, and R'$_5$ are respectively a phenyl, heterocyclic, or benzene-condensed heterocyclic group which is substituted by a carbonyl group; T is a group of aminocarbonyl, carbonylamino, carbonyloxy, oxycarbonyl, or the like) are disclosed in Japanese Kohyo 4-500664 (WO9002746), and specific examples thereof include compounds having, as the bridging moiety, a carbonylbis(imino-1H-indole-2-carbonyl) group, 5,5'-[(1,2-dioxo-1,2-ethanediyl)dia mino]bis-1H-indole-2-carbonyl group, or the like.

A compound having two 7-trifluoromethyl-8-methoxycarbonyl-1,2,3,6-tetrahydropyrrolo[3,2-e]indole rings and carbonylbis(imino-1-H-indole-2-carbonyl) group as a bridging moiety is disclosed by the inventors of the present invention (JP-A-6-116269).

However, the acrylamide derivatives of the present invention are not known.

The clinical therapy for cancer includes surgical resection, radiotherapy with X-rays or the like, and chemotherapy with a chemotherapeutic. Of these therapies, only the chemotherapy with a chemotherapeutic is effective against the cancers having spread over various parts of the body, and terminal cancers. The chemotherapy, which is considered intrinsically to impose less burden to the patient, causes actually serious pains to the patient owing to the adverse strong side effects. Although most of the current chemotherapeutics are effective against leukemia exhibiting rapid cell growth, they are less effective against solid cancer exhibiting slow cell growth. Therefore, the chemotherapy is not preferentially conducted for cancer therapy.

In such a situation of chemotherapy, the present invention intends to provide a compound which is effective selectively against cancer cells, effective also against solid tumors, and yet less toxic.

DISCLOSURE OF THE INVENTION

After comprehensive investigation to solve the above problems, a novel compound was found, by the inventors of the present invention, which is effective selectively against cancer cells, less toxic, and effective also against solid tumors.

The present invention provides acrylamide derivatives, optical isomers thereof, and pharmaceutically acceptable salts thereof, and a process for production thereof; the acrylamide derivatives being represented by General Formula (1):

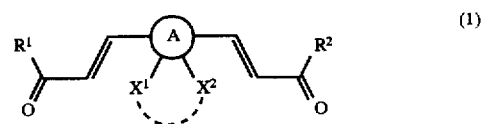

(wherein $X^1$ and $X^2$ are independently a hydrogen atom, a halogen atom, an amino group, an alkylamino group, an aminoalkyl group, a hydroxyl group, $OR^3$ ($R^3$ being a linear or branched lower alkyl of C1–C6, or a substituted or unsubstituted aryl group), $OCOR^3$ ($R^3$ being the same as above), or a linear or branched lower alkyl of C1–C6, and $X^1$ and $X^2$ may be linked together; the ring A is a pyrrole ring, a furan ring, a thiophene ring, a benzene ring, a pyridine ring, a pyridazine ring, a pyrimidine ring, a pyrazine ring, a biphenyl ring, a bipyridine ring, a bipyrimidine ring, a naphthalene ring, an anthracene ring, or an anthraquinone ring; and $R^1$ and $R^2$ are independently:

a.

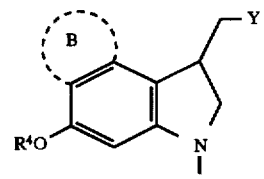

($R^4$ is a hydrogen atom, a protecting group for hydroxyl, or a substituent decomposable in vivo; Y is a halogen atom, an arylsulfonyloxy group, a lower alkylsulfonyloxy group, a haloalkylsulfonyloxy group, or an azide group;

b.

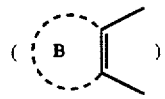

is a condensed ring, or

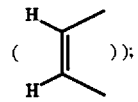

b.

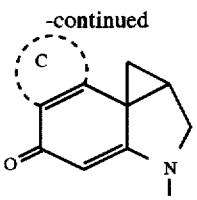

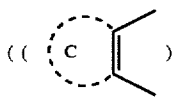

is a condensed ring or

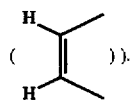

Of the substituents defined as $X^1$ and $X^2$, the halogen atom includes a fluorine atom, a chlorine atom, a bromine atom, and an iodine atom; the alkylamino group includes linear or branched C1–C6 alkyl-substituted amino group such as methylamino, dimethylamino, ethylamino, diethylamino, isopropylamino, and diisopropylamino; the aminoalkly group includes linear or branched C1–C6 alkyl group having an amino group bonded thereto such as aminomethyl, 1-aminoethyl, 2-aminoethyl, 1-aminoisopropyl, 2-aminopropyl, and 3-aminopropyl; the substituted or unsubstituted aryl group includes unsubstituted aryl groups and aryl groups substituted with a halogen atom, an alkyl group, an amino group, an alkylamino group, an aminoalkyl group, a hydroxyl group, or the like such as chlorophenyl, methylphenyl, aminophenyl, methylaminophenyl, aminomethylphenyl, and hydroxyphenyl.

The wording "$X^1$ and $X^2$ which may be linked together" means an alkylene chain condensed with the ring A or an alkylene ring containing one or two oxygen atoms, amino groups, an ester group, or a carbamoyl group, and bonded to the ring A, the example including:

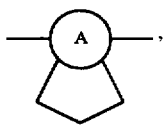

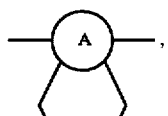

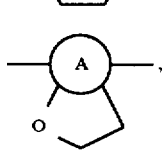

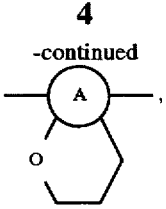

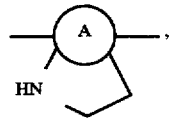

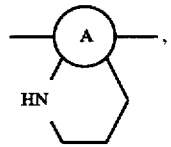

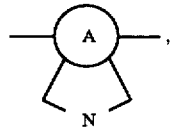

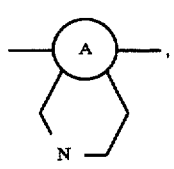

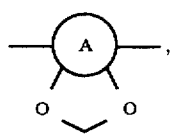

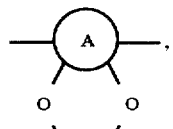

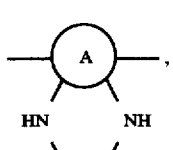

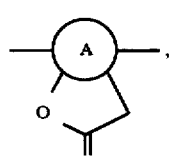

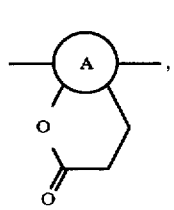

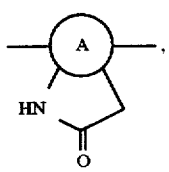

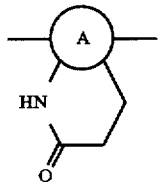

and

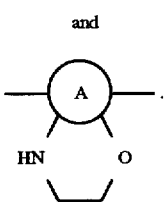

The condensed ring represented by b.

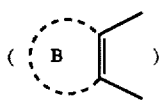

and

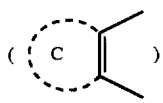

includes condensed aromatic or nonaromatic hydrocarbon rings or heterocyclic condensed rings such as

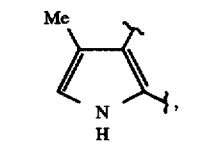

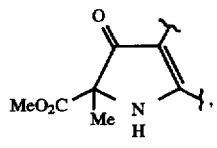

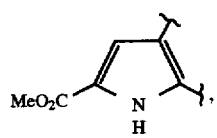

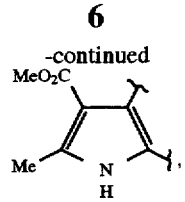

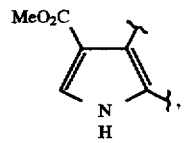

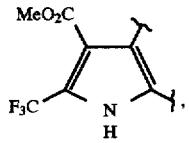

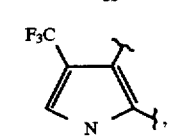

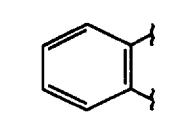

and

The wording "substituent decomposable in vivo" means a substituent giving a hydroxyl group by decomposition in vivo, including lower alkanoyl groups, aryloyl groups, lower alkoxycarbonyl groups, substituted or unsubstituted aryloxycarbonyl groups, substituted or unsubstituted carbamoyl groups, and acyl residues of α-amino acids.

The lower alkanoyl groups include specifically formyl, acetyl, propionyl, butyryl, pivaloyl, valeryl, and caproyl. The aryloyl groups include specifically benzoyl, phenylacetyl, and naphtoyl. The lower alkoxycarbonyl groups include specifically methoxycarbonyl, ethoxycarbonyl, propoxycarbonyl, butoxycarbonyl, and hexyloxycarbonyl. The substituted or unsubstituted aryloxycarbonyl groups include phenoxycarbonyl, p-chlorophenoxycarbonyl, p-methoxyphenoxycarbonyl, p-aminophenoxycarbonyl, benzyloxycarbonyl, p-chlorobenzyloxycarbonyl, p-methoxybenzyloxycarbonyl, and p-aminobenzyloxycarbonyl. The substituted or unsubstituted carbamoyl groups include specifically N-lower alkylcarbamoyl, N,N-di-lower alkylcarbamoyl, N-arylcarbamoyl, pyrrolidinylcarbonyl, or substituted pyrrolidinylcarbonyl such as 3-(dimethylamino) pyrrolidinylcarbonyl; substituted or unsubstituted piperidinylcarbonyl such as 4-(dimethylamino)piperidinylcarbonyl and (4-piperidinopiperidinyl)carbonyl; substituted or unsubstituted 1-piperazinylcarbonyl such as (4-methyl-1-piperazinyl)carbonyl [4-[2-(dimethylamino)ethyl]-1-piperazinyl]carbonyl, [4-(2-(hydroxyethyl)-1-piperazinyl] carbonyl, and [4-[2-[2-(dimethylamino) ethoxy]-1-ethyl]-1-piperazinyl]carbonyl; substituted or unsubstituted 1-morpholinylcarbonyl and pyrrolidinylcarbonyl; and alkyl-substituted silyl. The acyl residues of α-amino acids include acyl residues of glycine, alanine valine,leucine, isoleucine, serine, threonine, cysteine, methionine, aspartic acid, glutamic acid, asparagine, glutamine, lysine, arginine, phenylalanine, tyrosine, histidine, tryptophane, proline, and hydroxyproline with the amino group unprotected or protected by benzyloxycarbonyl, fluorenylmethyloxycarbonyl, t-butoxycarbonyl, or the like.

The arylsulfonyloxy groups include specifically benzenesulfonyloxy, and toluenesulfonyloxy. The lower alkylsulfonyl groups include methanesulfonyloxy, ethanesulfonyloxy, and propanesulfonyloxy. The haloalkylsulfonyloxy groups include specifically trifluoromethanesulfonyloxy, and trichloromethanesulfonyloxy.

EMBODIMENTS OF THE INVENTION

The present invention provides a compound represented by General Formula (1) above produced through the process described below.

A carboxylic acid represented by General Formula (2a):

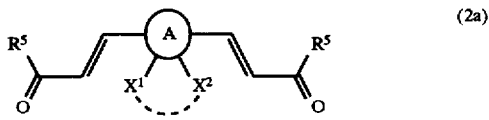
(2a)

(where $R^5$ is OH; the ring A, $X^1$ and $X^2$ are the same as above) is condensed with a compound represented by General Formula (4) or (5), or a salt thereof:

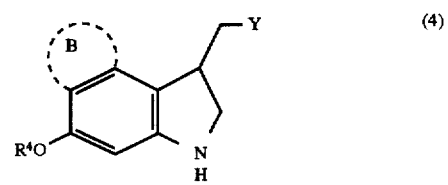
(4)

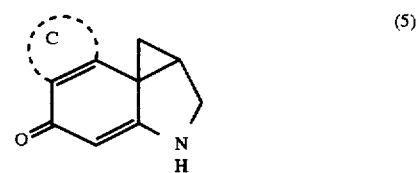
(5)

(where

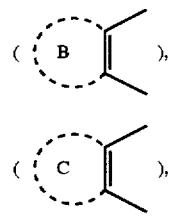

$R^4$, and Y are the same as above) by use of a condensing agent such as dicyclohexylcarbodiimide (DCC) and 3-ethyl-1- (3-dimethylaminopropyl) carbodiimide hydrochloride. Otherwise, a carboxylic acid halide, a carboxylic acid imidazolide, an active ester of the carboxylic acid, or a mixed or symmetric acid anhydride represented by Formula (2b):

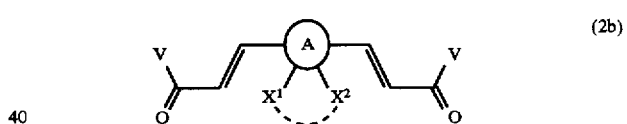
(2b)

(where V is a reactive residue such as a halogen atom, 1-imidazolyl, 4-nitrophenoxy, and succinimidoyloxy) is allowed to react with the above compound. Thereby a compound represented by General Formula (1a) or (1b) is produced:

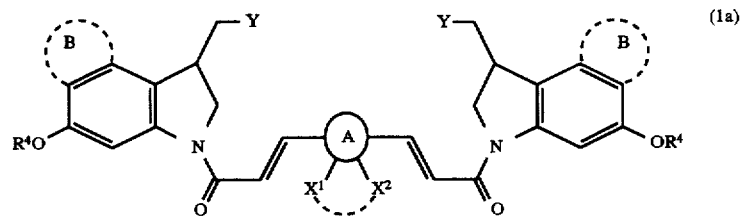
(1a)

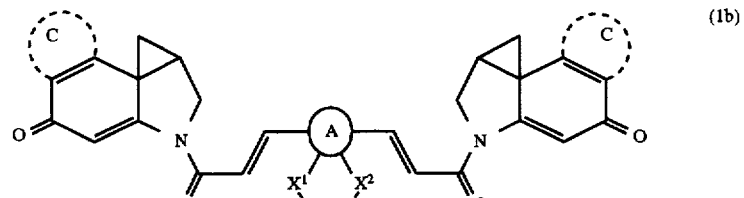
(1b)

(where the ring A.

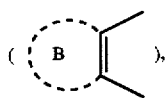

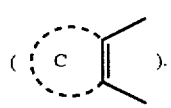

$R^4$, $X^1$, $X^2$, and Y are the same as above). The condensation reaction can readily be conducted in the presence or absence of an organic base such as triethylamine, diisopropylethylamine, pyridine, and dimethyaminopyridine; or an inorganic base such as sodium hydrogen carbonate, potassium carbonate, sodium hydride, and potassium hydride in a solvent such as dichloromethane, toluene, acetonitrile, N,N-dimethylforamide, dimethylsulfoxide, and tetrahydrofuran, at a temperature ranging from −20° to 50° C. for a time ranging from 30 minutes to 48 hours.

In another method, a compound represented by General Formula (1c) below:

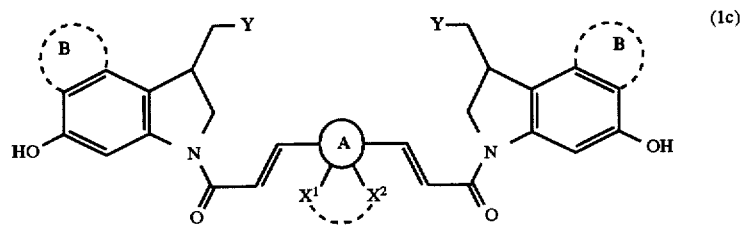

(where the ring A,

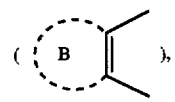

$X^1$, $X^2$, and Y are the same as above) is treated with a lower alkanoyl chloride, an aryloyl chloride, a lower alkoxycarbonyl chloride, a substituted or unsubstituted aryloxycarbonyl chloride, an α-amino acid chloride, a substituted or unsubstituted carbamoyl chloride, or an active ester thereof to obtain a compound represented by General Formula (1d):

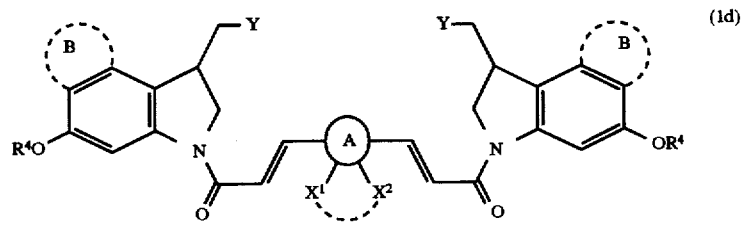

(where the ring A,

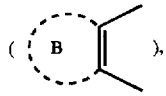

$R^4$, $X^1$, $X^2$, and Y are the same as above). This reaction is conducted in the presence or absence of an organic base such as triethylamine, diisopropylethylamine, pyridine, and dimethylaminopyridine; or an inorganic base such as sodium hydrogendarbonate, and potassium carbonate, in an inert solvent at a temperature ranging from −20° to 100° C., preferably 0° to 50° C.

Further, the compound represented by General Formula (1c) can be converted to the compound represented by General Formula (1b) by a ring closure reaction in the presence of a base. This reaction is conducted by treating the compound represented by General Formula (1c) in the presence of 1 to 10 equivalent moles, preferably 1 to 5 equivalent moles of an organic base such as a diazabicyclo base, and triethylamine, or an inorganic base such as sodium hydroxide, sodium hydride, and potassium carbonate in an inert solvent such as dichloromethane, toluene, acetonitrile, N,N-dimethylformamide, dimethylsulfoxide, and tetrahydrofuran, or mixture thereof at −78° to 100° C., preferably from 0° to 50° C., for 10 minutes to 24 hours, preferably from 20 minutes to 5 hours. The compound represented by General Formula (1b) can be converted to the compound represented by General Formula (1c) by treatment in the presence of hydrogen chloride, hydrogen bromide, hydrochloric acid, hydrobromic acid, toluenesulfonic acid, benzenesulfonic acid, methanesulfonic acid, trifluoromethansulfonic acid, hydrogen azide acid, or the like in an inert solvent such as ethyl acetate, dichloromethane, acetonitrile, N,N-dimethylformamide, and tetrahydrofuran at a temperature ranging from −20° C. to the boiling point of the solvent, preferably from 0° to 50° C. For this reaction, use of the an excessive amount of the acid is preferred for shortening the reaction time.

Dialdehyde derivatives represented by General Formula (9):

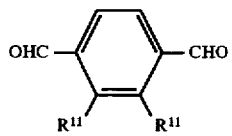

(9)

where $R^{11}$ is a linear or branched lower alkyl of C1–C6, and another dialdehyde represented by General Formula (7):

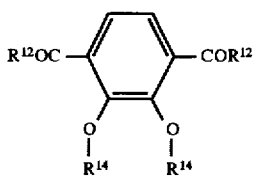

(7)

(where $R^{12}$ is $OR^{13}$ ($R^{13}$ being a linear or branched lower alkyl of C1–C6), or a dialkylamino group; $R^{14}$ is a linear or branched lower alkyl of C1–C6, or two $R^{14}$ groups are linked together to form a methylene, ethylene, or propylene group to form a ring) can be produced through the steps shown below:

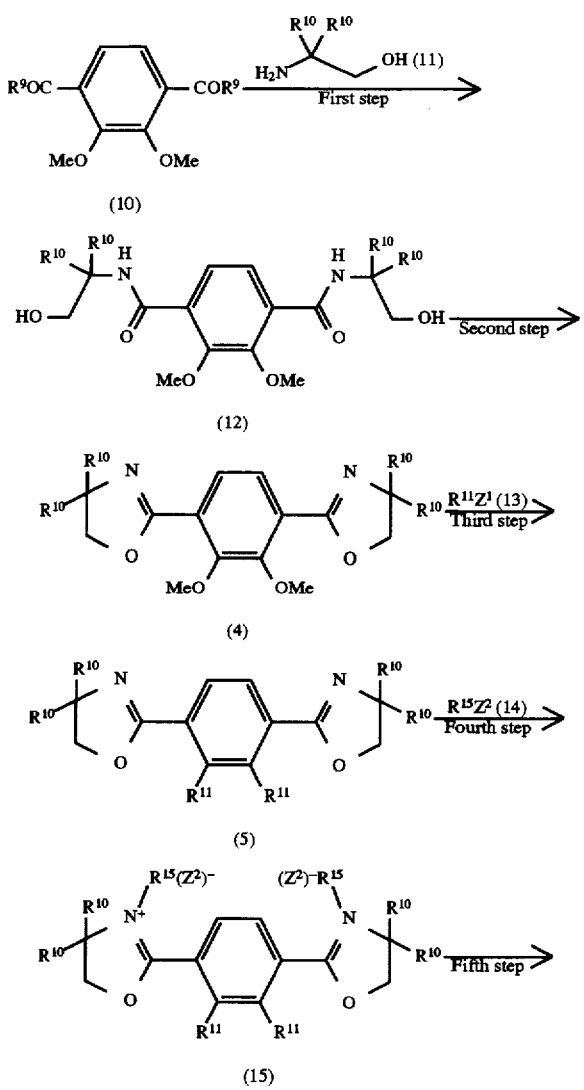

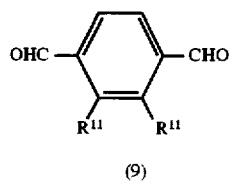

(9)

(where $R^9$ is a hydroxly group or a reactive residue; $R^{10}$ is a hydrogen atom, or a linear or branched lower alkyl of C1–C6; $R^{15}$ is methyl, ethyl, or benzyl; and $R^{11}$ is the same as above).

(First Step)

In this step, the compound represented by General Formula (10) is condensed with the compound represented by General Formula (11) to produce the compound represented by General Formula (12).

This reaction can be conducted readily by condensation, when $R^9$ is OH, by use of a condensation agent such as dicyclohexylcarbodiimide (DCC), and 3-ethyl-1-(3-diemthylaminopropyl)carbodiimide hydrochloride, or, when $R^9$ is a reactive residue such as a halogen atom, in the presence or absence of a base such as pyridine, triethylamine, and diisopropylethylamine.

(Second Step)

In this step, the compound represented by General Formula (12) is treated for ring closure to produce the compound represented by General Formula (4). The ring closure reaction is conducted by treatment with polyphosphoric acid, polyphosphoric acid ester, sulfuric acid, thionyl chloride, or the like at a temperature of from 0° to 100° C. for 30 minutes to 24 hours.

(Third Step)

In this step, the compound represented by General Formula (4) is allowed to react with an organometallic reagent represented by General Formula (13) below:

$$R^{11}Z^1 \qquad (13)$$

(where $Z^1$ is Li, MgCl, or MgBr; and $R^{11}$ is the same as above) to produce a compound represented by General Formula (5). This reaction can readily be conducted by treatment in a solvent such as tetrahydrofuran, diethyl ether, dimethoxyethane, toluene, and hexane, or a mixture thereof at a temperature of ranging from −20° to 50° C. for a time ranging from 30 minutes to 24 hours.

(Fourth Step)

In this step, the compound represented by General Formula (5) is allowed to react with the compound represented by General Formula (14):

$$R^{15}Z^2 \qquad (14)$$

(where $Z^2$ is Cl , Br, I, $OSO_2CH_3$, or

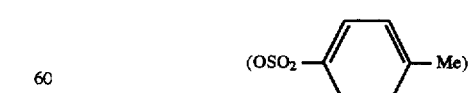

and $R^{15}$ is the same as above). This reaction can readily be conducted in a solvent such as nitromethane, dimethylformamide, and dioxane, or without a solvent at a temperature ranging from 0° to 100° C. for a time of from 30 minutes to 24 hours.

(Fifth Step)

In this step, the compound represented by General Formula (15) is reduced to produce the dialdehyde derivatives represented by General Formula (9). The reducing agent for this reaction includes diisobutylaluminum hydride, lithium aluminum hydride, sodium bis(methoxyethoxy)aluminum hydride, sodium boronhydride, sodium cyanoborohydride, and lithium boron hydride. The reaction is conducted in toluene, ether, diglyme, tetrahydrofuran, methanol, or ethanol, or a mixture thereof, and proceeds smoothly at a temperature ranging from −78° C. to 50° C.

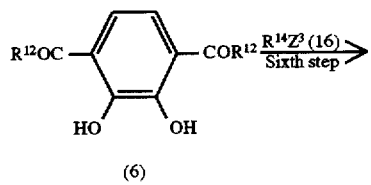

(6)

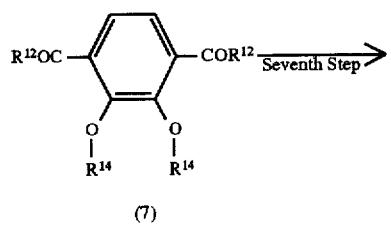

(7)

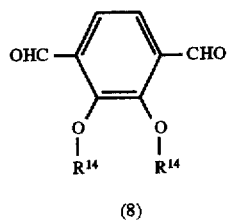

(8)

In this step, the phenol derivatives represented by General Formula (6) is alkylated by the compound represented by General Formula (16) below:

$$R^{14}Z^3 \quad (16)$$

(where $Z^3$ is Cl, Br, I, $OSO_2CH_3$, or

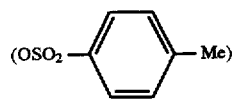

; $R^{14}$ is the same as above) in the presence of caesium carbonate to produce the compound represented by General Formula (7). The reaction can readily be conducted in a solvent such as dimethylformamide, dimethylacetamide, N-methylpyrrolidone, and dimethyl sulfoxide by use of 1 to 5 equivalents, preferably 2 equivalents of caesium carbonate, at a temperature ranging from 0° to 100° C. for a time of 30 minutes to 24 hours.

(Seventh Step)

In this step, the compound represented by General Formula (7) is reduced to produce the dialdehyde derivatives represented by General Formula (8). The reducing agent for this reaction includes diisobutylaluminum hydride, lithium aluminum hydride, sodium bis(methoxyethoxy)aluminum hydride, and, sodium bis(2-methoxyethoxy)aluminum hydride/N-methylpiperazine, and the like. This reaction is conducted in toluene, ether, diglyme, tetrahydrofuran, or the like, or mixture thereof. The reaction proceeds smoothly at a temperature of −78° to 50° C.

$R^{10}$, which is a linear or branched lower alkyl group of C1–C6, includes specifically methyl, ethyl, propyl, butyl, and isopropyl.

$R^{11}$, which is a linear or branched lower alkyl group of C1–C6, includes specifically methyl, ethyl, propyl, butyl, and isopropyl.

$R^{13}$, which is a linear or branched lower alkyl group of C1–C6, includes specifically methyl, ethyl, propyl, butyl, and isopropyl.

The dialkylamino group includes specifically dimethylamino, diethylamino, dibutylamino, diisopropylamino, pyrrolidinyl, and piperidinyl.

$R^{14}$, which is a linear or branched lower alkyl group of C1–C6, includes specifically methyl, ethyl, propyl, butyl, and isopropyl.

The compound, as the starting material in the present invention, represented by General Formula (2a) below:

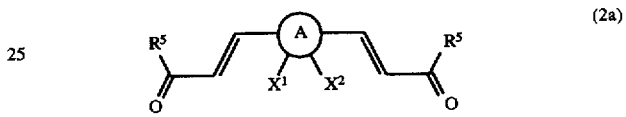

(2a)

where $X^1$, $X^2$, the ring A and $R^5$ are the same as above) is an important intermediate of the present invention, and can be produced by a method mentioned below as an example.

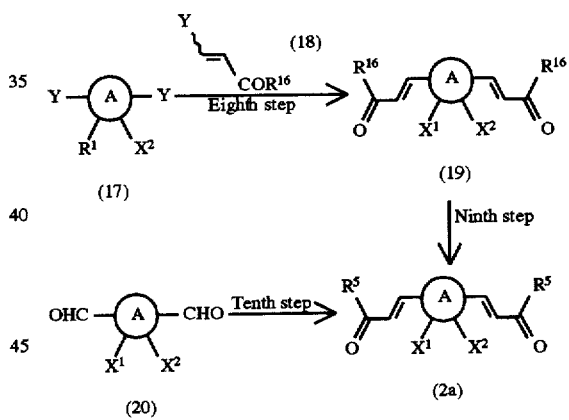

In this step, the compound represented by General Formula (17) (in the formula, $Y^1$ is Br, I, or $OSO_2CF_3$; $X^1$, $X^2$, and the ring A are the same as above) is allowed to react with the acrylic acid derivatives represented by General Formula (18) (in the formula, $R^{16}$ is methoxy, ethoxy, or benzyloxy; $y^2$ is hydrogen atom, trimethylstannyl, or tributylstannyl) in the presence of a palladium catalyst for cross-coupling to produce the diacrylic acid ester derivatives represented by General Formula (19). This reaction can be conducted by a known method (for example, "Jikken Kagaku Koza" (Textbook for Experimental Chemistry), 4th Edition, pp. 396–427, (1991), Maruzen).

(Ninth Step)

In this step, the diacrylic acid ester derivatives represented by General Formula (19) is de-esterified to produce the diacrylic acid derivatives represented by General Formula (2a). This reaction can be conducted by a known method ("Protective Groups in Organic Synthesis", pp. 231–265 (1991), John Wiley & Sons).

(Tenth Step)

In this step, the dialdehyde derivatives represented by General Formula (20) and malonic acid are condensed to produce the diacrylic acid derivatives represented by General Formula (2a). This reaction can be conducted by a known method.

The racemates, and the optically active isomers of the compounds represented by General Formulas (4) and (5) can be produced by a known method (for example, Tetrahedron Lett., Vol. 27, p. 4103 (1986); J. Med. Chem., Vol. 37, p. 232 (1994); BioMed. Chem. Lett., Vol. 2, p. 755 (1992); J. Am. Chem. Soc., Vol. 115, p. 9025 (1993); J. Org. Chem., Vol. 57, p. 2878 (1992); JP-A-3-128379; and JP-A-6-116269).

The compound represented by General Formula (1) is useful as an antimicrobial and antitumor composition singly or in combination with one or more known pharmaceutically acceptable adjuvants. It can be dosed orally in a form of tablets, capsules, powders, granules, or ampules, or parenterally.

The parenteral adminstration includes intravenous administration, intraarterial administration, intraperitoneal administration, hypodermic administration, intramuscular administration, intrathoracic administration, and topical administration.

A compound represented by General Formula (1) or a salt thereof, for example, is dissolved in physiological saline, or an aqueous solution of glucose, mannitol, lactose or the like to prepare an appropriate medical composition. Otherwise, a salt of the compound represented by General Formula (1) is freeze-dried in a conventional manner, and sodium chloride or the like is added thereto to prepare a powdery injection. This medical composition may contain a conventional additive for medicines, such as a pharmaceutically acceptable salt.

The dose of administration depends on the age, and the symptom of the patient, and is in the range of from 0.00001 to 100 mg/kg/day for mammals including humans. The administration is conducted, for example, once or several times a day, or intermittently one to five times a weak, or at intervals of two to four weeks.

The effectiveness of the present invention is described below by reference to Examples without limiting the invention thereto.

EXAMPLES

Example 1

To 13.5 mg (30 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate, was added 0.6 mL of 3M hydrogen chloride-ethyl acetate. The mixture was stirred at room temperature for one hour. Then the solvent was removed by distillation. The resulting residue was stirred with 3.3 mg (15 μmol) of 3,3'-(1,4-phenylene) diacrylic acid and 17.3 mg (90 μmol) of 1-(3-dimethylaminopropyl)-3-ethylcarbodiimide hydrochloride in 0.3 mL of anhydrous dimethylformamide under an argon stream overnight. Water was added to the reaction mixture, and the resulting mixture was extracted with chloroform-methanol (5:1). The extract was dried over anhydrous sodium sulfate. The solvent was removed by distillation and the residue was purified by silica gel column chromatography (chloroform:methanol:acetone=5:1:1) to obtain 3.3 mg (25%) of (S,S)-3,3'-[3,3'-(1,4-phenylenediacryloyl)]-bis[1-chlorome thyl-5-hydroxy-7-trifluoromethyl-1,2,3,6-tetrahydropyrrolo[3,2-e]indole-8-methoxycarbonyl] in a yellow crystal state.

$[\alpha]^{24}_D$=−144° (c=0.20, tetrahydrofuran); NMR (DMSO $d_6$) δ: 3.48(2H,t,J=8 Hz), 3.83(2H,d,J=8 Hz), 3.88(6H,s), 4.28(2H,br), 4.40–4.49(4H,m), 7.30(2H,d,J=15 Hz), 7.70 (2H,d,J=16 Hz), 7.87(4H,s), 8.11(2H,brs), 10.52(2H,br), 13.02(2H,br)

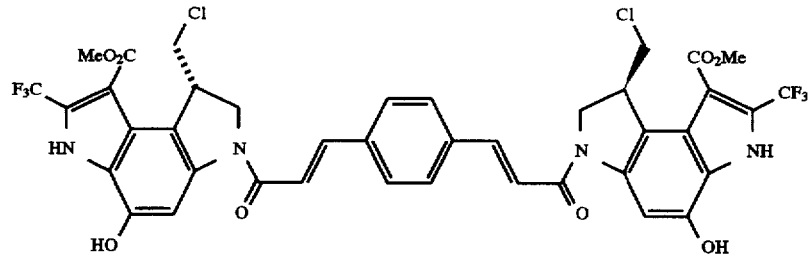

Example 2

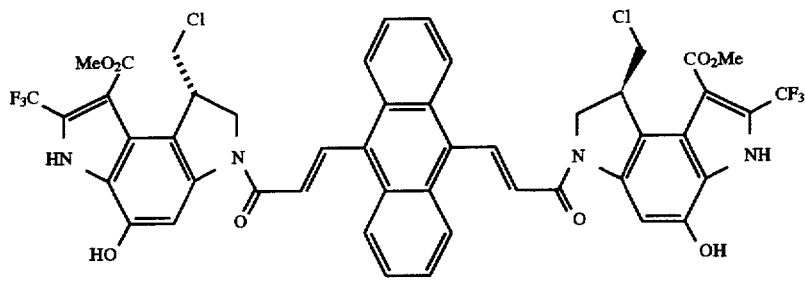

To 13.5 mg (30 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate, was added 0.43 mL of 3M hydrogen chloride-ethyl acetate. The mixture was stirred at room temperature for 2 hours. Then the solvent was removed by distillation. The resulting residue was stirred with 4.8 mg (15 μmol) of 3,3'-(9,10-anthracenediyl) diacrylic acid and 17.3 mg (90 μmol) of 1-(3-dimethylaminopropyl)-3-ethylcarbodiimide hydrochloride in 0.3 mL of anhydrous dimethylformamide under an argon stream overnight. Water was added to the reaction mixture, and the resulting precipitate was purified by silica gel column chromatography (tetrahydrofuran:chloroform=2:1) to obtain 3.7 mg (25%) of (S,S)-3,3'-[3,3'-(9,10-anthracenediyl)diacryloyl]-bis[1-chloromethyl-5-hydroxy-7-trifluoromethyl-1,2,3,6-tetrahydropyrrolo [3,2-e]indole-8-methoxycarbonyl] in a yellow crystal state.

$[\alpha]_D^{29}$=−144° (c=0.20, tetrahydrofuran); NMR (DMSO $d_6$) δ: 3.56(2H,t,J=10 Hz), 3.79–3.85(2H,m), 3.87(6H,s), 4.22–4.29(2H,m), 4.33–4.47(4H,m), 7.05(2H,d,J=16 H) z), 7.66(4H,dd,J=4 and 7 Hz), 8.22(2H,s), 8.37(4H,dd,J=7 and 4 Hz), 8.55(2H,d,J=16 Hz), 10.64(2H,s), 13.11(2H,s).

In a similar manner, 2.5 mg (15%) of (S,S)-3,3'-[3,3'-(5,8-dimethoxy-1,4-naphthalenediyl) diacryloyl]-bis[1-chloromethyl-5-hydroxy-7-trifluoromethyl-1,2,3,6-tetrahydropyrrolo [3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo [3,2-e]indole-8-carboxylate and 4.9 mg (15 μmol) of 3,3'-(5,8-dimethoxy-1,4-naphthalenediyl)-diacrylic acid.

$[\alpha]_D^{30}$=−56° (c=0.05, tetrahydrofuran); NMR (DMSO $d_6$) δ: 3.52(2H,dd,J=9 and 11 Hz), 3.80–3.87(2H,m), 3.88 (6H,s), 3.89(6H,s), 4.23–4.31(2H,m), 4.40–4.47(4H,m), 6.77(2H,d,J=15 Hz), 7.10(2H,s), 7.75(2H,s), 8.16(2H,s), 8.77(2H,d,J=15 Hz), 10.54(2H,s), 13.06(2H,s).

Example 3

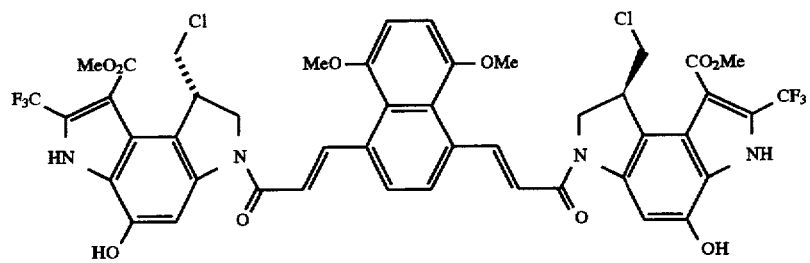

Example 4

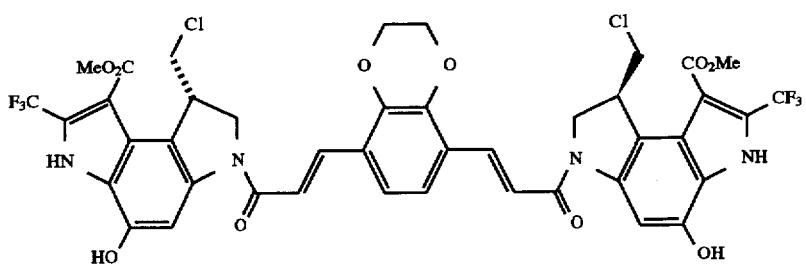

In a similar manner, 4.1 mg (15%) of (S,S)-3,3'-[3,3'-(2,3-(ethylenedioxy) -1,4-phenylene) diacryloyl]-bis[1-chloromethyl-5-hydroxy-7-trifluoromethyl-1,2,3,6-tetrahydropyrrolo [3,2-e]indole-8-methoxycarbonyl] was obtained from 26.9 mg (60 μmol) of methyl (S)-3-t-butoxycarbonyl-1-chloromethyl-5-hydroxy-7-trifluoromethyl-1,2,3,6-tetrahydropyrrolo[3, 2-e]indole-8-carboxylate and 8.3 mg (30 μmol) of 3,3'-(2,3-(ethylenedioxy)-1,4-phenylene)diacrylic acid.

$[\alpha]_D^{30}$=−12° (c=0.05 tetrahydrofuran); NMR (DMSO $d_6$) δ: 3.51(2H,t,J=10 Hz), 3.79–3.85(2H,m), 3.88(6H,s), 4.23–4.32(2H,m), 4.38–4.44(4H,m), 4.46(4H,s), 7.25(2H,d, J=16 Hz), 7.52(2H,s), 7.89(2H,d,J=16 Hz), 8.10(2H,s), 10.56(2H,s), 13.07(2H,s).

Example 5

In a similar manner, 5.5 mg (20%) of (S,S)-3,3'-[3,3'-(2,3-diethyl-1,4-phenylene)diacryloyl]-bis[1-chloromethyl-5-hydroxy-7-trifluoromethyl-1,2,3,6-tetrahydropyrrolo[3,2-e] indole-8-methoxycarbonyl] was obtained from 26.9 mg (60 μmol) of methyl (S)-3-t-butoxycarbonyl-1-chloromethyl-5-hydroxy-7 trifluoromethyl-1,2,3,6-tetrahydropyrrolo[3,2-e] indole-8-carboxylate and 8.2 mg (30 μmol) of 3,3'-(2,3-diethyl-1,4-phenylene) diacrylic acid.

$[\alpha]_D^{31}$=−16° (c=0.05, tetrahydrofuran); NMR (DMSO $d_6$) δ: 1.18(6H,t,J=8 Hz), 2.85(4H,q,J=8 Hz), 3.51(2H,t,J=10 Hz), 3.72–3.85(2H,m), 3.88(6H,s), 4.22–4.32(2H,m), 4.38–4.48(4H,m), 7.12(2H,d,J=16 Hz), 7.78(2H,s), 7.99 (2H,d,J=16 Hz), 8.11(2H,s), 10.54(2H,s), 13.06(2H,s).

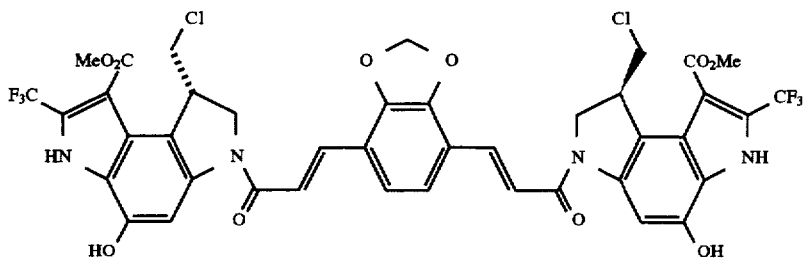

In a similar manner, 2.4 mg (17%) of (S,S)-3,3'-[3,3'-(2, 3-(methylenedioxy)-1,4-phenylene) diacryloyl]-bis[1-chloromethyl-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate and 3.9 mg (15 μmol) of 3,3'-(2,3-(methylenedioxy)-1,4-phenylene)diacrylic acid.

$[\alpha]_D^{30}$=−12° (c=0.05, tetrahydrofuran); NMR (DMSO $d_6$) δ: 3.52(2H,dd,J=9 and 11 Hz), 3.78–3.85(2H,m), 3.88 (6H,s), 4.24–4.32(2H,m), 4.32–4.45(4H,m), 6.38(2H,s), 7.28(2H,d,J=16 Hz), 7.37(2H,s), 7.65(2H,d,J=16 Hz), 8.10 (2H,s), 10.58(2H,s), 13.17(2H,s).

Example 6

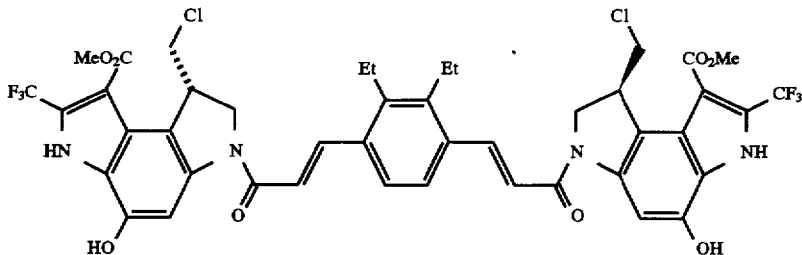

60

Example 7

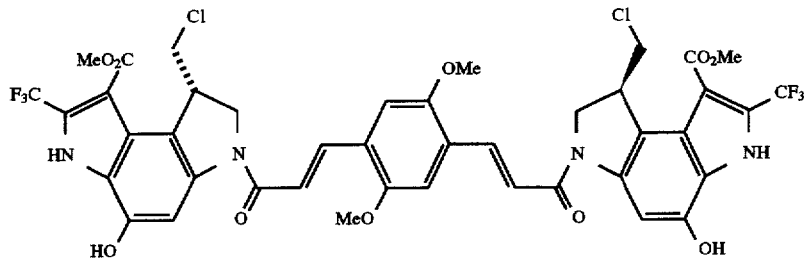

In a similar manner, 2.1 mg (15%) of (S.S)-3,3'-[3,3'-(2,5-dimethoxy-1,4-phenylene) diacryloyl]-bis[1-chloromethy 1-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo [3,2-e]indole-8-carboxylate and 4.2 mg (15 μmol) of 3,3'-(2,3-dimethoxy-1,4-phenylene)diacrylic acid.

$[\alpha]_D^{32}$=–56° (c=0.05, tetrahydrofuran); NMR (DMSO $d_6$) δ: 3.52(2H,dd,J=8 and 11 Hz), 3.78–3.90(2H,m), 3.88 (6H,s), 3.98(6H,s), 4.23–4.33(2H,m), 4.38–4.48(4H,m), 7.30(2H,d,J=16 Hz), 7.53(2H,s), 7.96(2H,d,J=16 Hz), 8.10 (2H,s), 10.56(2H,s), 13.07(2H,s).

Example 8

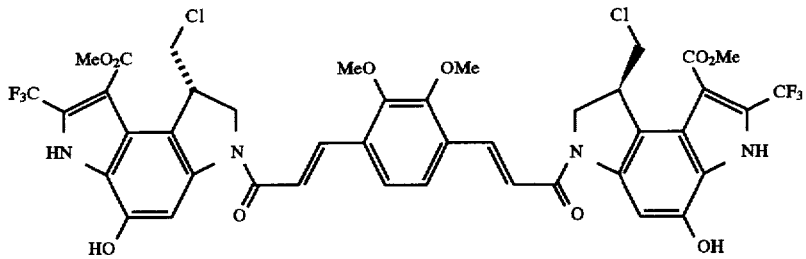

In a similar manner, 1.1 mg (8%) of (S,S)-3,3'-[3,3'-(2,3-dimethoxy-1,4-phenylene)diacryloyl]-bis[1-chloromethy 1-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3, 6-tetrahydropyrrolo[3,2-e]indole-8-carboxylate and 4.2 mg (15 μmol) of 3,3'-(2,5-dimethoxy-1,4-phenylene)diacrylic acid.

$[\alpha]_D^{32}$=–26° (c=0.05, tetrahydrofuran); NMR (DMSO $d_6$) δ: 3.51(2H,dd,J=9 and 10 Hz), 3.79–3.94(2H,m), 3.88 (6H,s), 3.90(6H,s), 4.24–4.33(2H,m), 4.39–4.49(4H,m), 7.31(2H,d,J=16 Hz), 7.78(2H,s), 7.88(2H,d,J=16 Hz), 8.11 (2H,s), 10.57(2H,s), 13.08(2H,s).

Example 9

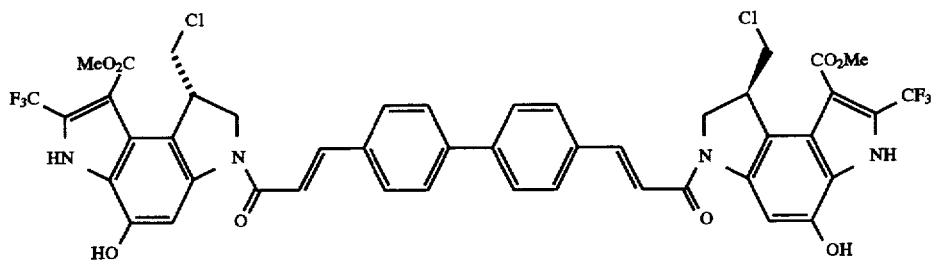

In a similar manner, 1.7 mg (12%) of (S,S)-3,3'-[3,3'-(1,1'-diphenyl-4,4'-diyl)diacryloyl]-bis[1-chloromethyl-5-hydroxy-7-trifluoromethyl-1,2,3,6-tetrahydropyrrolo [3,2-e] indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo [3,2-e]

indole-8-carboxylate and 4.4 mg (15 μmol) of 3,3'-(1,1'-diphenyl-4,4'-diyl)diacrylic acid.

$[\alpha]_D^{32}$=−36° (c=0.05, tetrahydrofuran); NMR (DMSO $d_6$) δ: 3.50(2H,dd,J=9 and 11 Hz), 3.78–3.90(2H,m), 3.88 (6H,s), 4.23–4.32(2H,m), 4.38–4.52(4H,m), 7.29(2H,d,J=15 H) z), 7.71(2H,d,J=15 Hz), 7.84(4H,d,J=8 Hz), 7.93(4H,d, J=8 Hz), 8.11(2H,s), 10.56(2H,s), 13.07(2H,s).

In a similar manner, 2.3 mg (16%) of (S,S)-3,3'-[3,3'-(1,4-anthracenediyl)diacryloyl]-bis[1-chloromethyl-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo[3,2-e]

Example 10

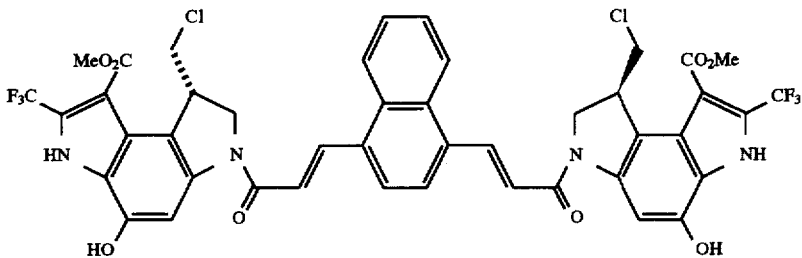

In a similar manner, 3.0 mg (22%) of (S,S)-3,3'-[3,3'-(1,4-naphthalenediyl)diacryloyl]-bis[1-chloromethyl-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate and 4.0 mg (15 μmol) of 3,3'-(1,4-naphthalenediyl)diacrylic acid.

$[\alpha]_D^{32}$=−41° (c=0.05, tetrahydrofuran); NMR (DMSO $d_6$) 67 : 3.53(2H,t,J=10 Hz), 3.78–3.92(2H,m), 3.88(6H,s), 4.25–4.34(2H,m), 4.45–4.54(4H,m), 7.36(2H,d,J=15 H) z), 7.74(2H,dd,J=3 and 6 Hz), 8.16(2H,s), 8.20(2H,s), 8.36(2H, dd,J=6 and 3 Hz), 8.51(2H,d,J=15 Hz) 10.60(2H,s), 13.09 (2H,s).

indole-8-carboxylate and 4.8 mg (15 μmol) of 3,3'-(1,4-anthracenediyl)diacrylic acid.

$[\alpha]_D^{32}$=−36° (c=0.05, tetrahydrofuran); NMR (DMSO $d_6$) δ: 3.54(2H,t,J=10 Hz), 3.78–3.93(2H,m), 3.89(6H,s), 4.27–4.36(2H,m), 4.46–4.57(4H,m), 7.43(2H,d,J=15 H) z), 7.62(2H,dd,J=3 and 6 Hz), 8.19(4H,s), 8.30(2H,dd,J=6 and 3 Hz), 8.67(2H,d,J=15 Hz), 9.04(2H,s), 10.60(2H,s), 13.07 (2H,s).

Example 11

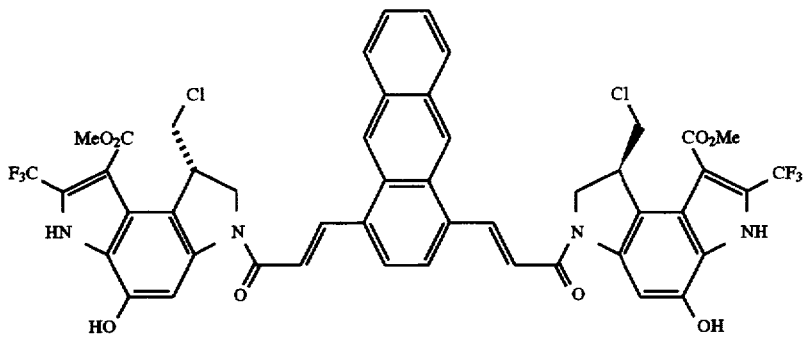

Example 12

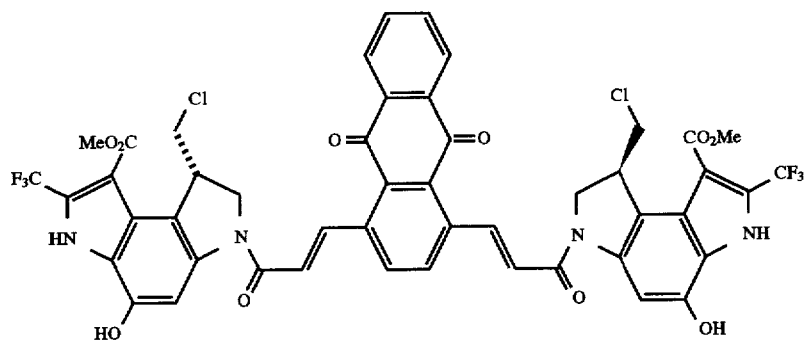

In a similar manner, 1.6 mg (4%) of (S,S)-3,3'-[3,3'-(9,10-dihydro-9,10-dioxo-1,4-anthracenediyl)diacryloyl]-bis[1-chloromethyl-5-hydroxy-7-trifluoromethyl-1,2,3,6-tetrahydropyrrolo[3,2-e]indole-8-methoxycarbonyl] was obtained from 40.4 mg (90 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate and 15.7 mg (45 μmol) of 3,3'-(9,10-dihydro-9,10-dioxo-1,4-anthracenediyl)diacrylic acid.

$[\alpha]_D^{32}$=−48° (c=0.05, tetrahydrofuran); NMR (DMSO $d_6$) δ: 3.53(2H,dd,J=9 and 10Hz), 3.79–3.91(2H,m), 3.88 (6H,s), 4.24–4.34(2H,m), 4.41–4.51(4H,m),, 7.11(2H,d,J= 16 H) z), 7.95(2H,dd,J=3 and 6 Hz), 8.10–8.19(4H,m), 8.21(2H,s), 8.53(2H,d,J=16 Hz), 10.61(2H,s), 13.10(2H,s).

chloromethyl-5-hydroxy-7-trifluoromethyl-1,2,3,6-tetrahydropyrrolo[3,2-e]indole-8-carboxylate and 4.4 mg (15 μmol) of 3,3'-(2,2'-bipyridyl-5,5'-diyl)diacrylic acid.

$[\alpha]_D^{32}$=−35° (c=0.05, tetrahydrofuran); NMR (DMSO $d_6$) δ: 3.51(2H,dd,J=9 and 10 Hz), 3.77–3.92(2H,m), 3.88 (6H,s), 4.25–4.33(2H,m), 4.39–4.55(4H,m), 7.47(2H,d,J=15 H) z), 7.78(2H,d,J=15 Hz), 8.13(2H,s), 8.51(4H,s), 9.08(2H, s) 10.60(2H,s), 13.09(2H,s)

Example 13

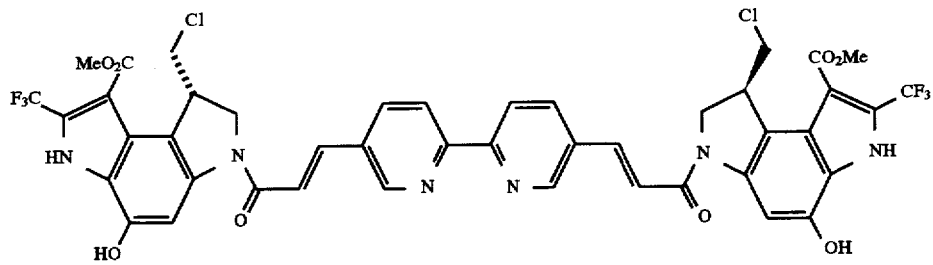

In a similar manner, 2.4 mg (17%) of (S,S)-3,3'-[3,3'-(2,2'-bipyridyl-5,5'-diyl)diacryloyl]-bis[1-chloromethyl-5-hydroxy-7-trifluoromethyl-1,2,3, 6-tetrahydropyrrolo [3,2-e]indole-8-methoxycarbonyl] was obtained from 13.5 mg (30 μmol) of methyl (S)-3-t-butoxycarbonyl-1-

Example 14

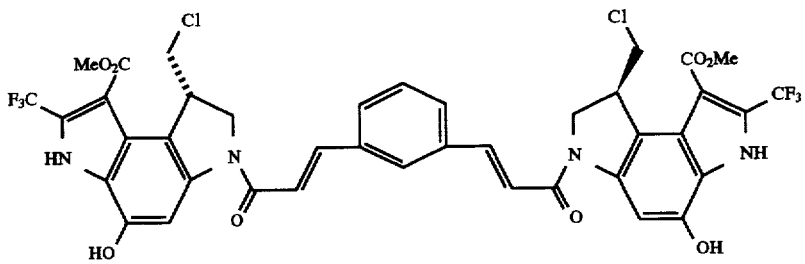

In a similar manner, 3.5 mg (27%) of (S,S)-3,3'-[3,3'-(1,3-phenylene)diacryloyl]-bis[1-chloromethyl-5-hydroxy-7-trifluoromethyl-1,2,3,6-tetrahydropyrrolo[3,2-e]indole-8-methoxycarbonyl] was obtained from 13.5 mg (30 μmol) of methyl (S) -3-t-butoxycarbonyl-1-chloromethyl-5-hydroxy- 7-trifluoromethyl-1,2,3,6-tetrahydropyrrolo [3,2-e]indole-8-carboxylate and 3.3 mg (15 μmol) of 3,3'-(1,3-phenylene) diacrylic acid.

$[\alpha]_D^{27}$=−28° (c=0.05, tetrahydrofuran); NMR (DMSO d$_6$) δ: 3.51(2H,dd,J=9 and 10 Hz), 3.75–3.93(2H,m.), 3.88 (6H,s), 4.24–4.33(2H,m), 4.38–4.53(4H,m), 7.33(2H,d,J=16 H) z), 7.52(1H,t,J=8 Hz), 7.73(2H,d,J=16 Hz), 7.88(2H,d, J=8 Hz), 8.12(2H,s), 8.25(1H,s), 10.56(2H,s), 13.06(2H,s).

Example 15

In a similar manner, 3.1 mg (10%) of (S,S)-3,3'-[3,3'-(3, 3"-(1,1':4',1"-terphenyl))diacryloyl]-bis[1-chloromethy 1-5-hydroxy-7-trifluoromethyl-1,2,3,6-tetrahydropyrrolo [3,2-e] indole-8-methoxycarbonyl] was obtained from 27.0 mg. (60 μmol) of methyl (S)-3-t-butoxycarbonyl-1-chloromethyl-5-hydroxy-7-trifluoromethyl-1,2,3,6-tetrahydropyrrolo [3,2-e] indole-8-carboxylate and 11.2 mg (30 μmol) of 3,3'-(4,4'-(1,1':4'1"-terphenyl))diacrylic acid.

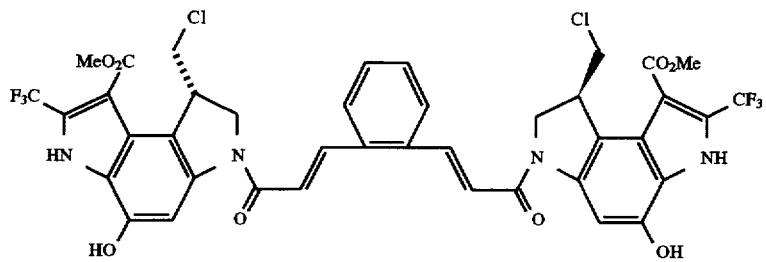

In a similar manner, 3.9 mg (30%) of (S,S)-3,3'-[3,3'-(1, 2-phenylene) diacryloyl]-bis[1-chloromethyl-5-hydroxy-7-trifluoromethyl-1,2,3,6-tetrahydropyrrolo[3,2-e]indole-8-methoxycarbonyl] was obtained from 13.5 mg (30 μmol) of methyl (S)-3-t-butoxycarbonyl-chloromethyl-5-hydroxy-7-trifluoromethyl-1,2,3,6-tetrahydropyrrolo[3,2-e]indole-8-carboxylate and 3.3 mg (15 μmol) of 3,3'-(1,2-phenylene) diacrylic acid.

$[\alpha]_D^{28}$=−107° (c=0.05, tetrahydrofuran); NMR (DMSO d$_6$) δ: 3.51(2H,t,J=9Hz), 3.75–3.92(2H,m), 3.87(6H,s), 4.22–4.32(2H,m), 4.38–4.50(4H,m), 7.16(2H,d,J=15 H) z), 7.52(2H,dd,J=4 and 6 Hz), 7.97(2H,m), 8.05(2H,d,J=15 Hz), 8.11(2H,s), 10.57(2H,s), 13.06(2H,s).

$[\alpha]_D^{28}$=−19° (c=0.05, tetrahydrofuran); NMR (DMSO d$_6$) δ: 3.51(2H,dd,J=9 and 10 Hz), 3.78–3.94(2H,m), 3.88 (6H,s), 4.24–4.34(2H,m), 4.39–4.54(4H,m), 7.37(2H,d,J=15 H) z), 7.58(2H,t,J=8 Hz), 7.78(2H,d,J=15 Hz), 7.81(2H,d, J=8 Hz) 7.83(2H,d,J=8 Hz), 7.92(4H,s), 8.13(2H,s), 8.18 (2H,s), 10.56(2H,s) 13.07(2H,s).

Example 16

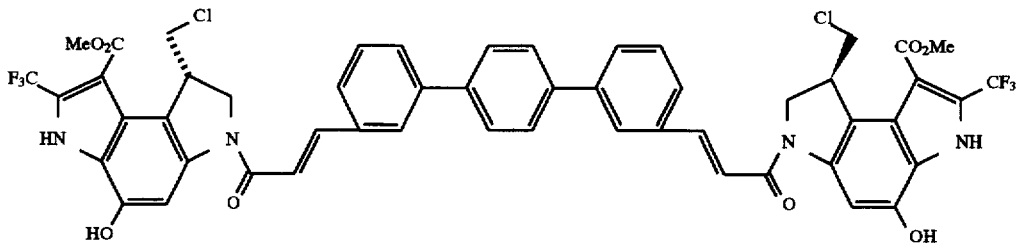

Example 17

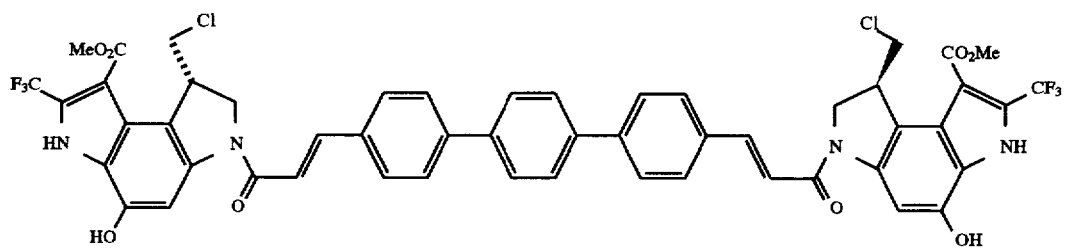

In a similar manner, 4.9 mg (32%) of (S,S)-3,3'-[3,3'-(4, 4"-(1,1':4',1"-terphenyl))diacryloyl]-bis[1-chloromethy 1-5-hydroxy-7-trifluoromethyl-1,2,3,6-tetrahydropyrrolo[3,2-e]indole-8-methoxycarbonyl] was obtained from 40.5 mg (180 μmol) of methyl (S)-3-t-butoxycarbonyl-1-chloromethyl-5-hydroxy-7-trifluoromethyl-1,2,3,6-tetrahydropyrrolo[3,2-e]indole-8-carboxylate and 5.6 mg (15 μmol) of 3,3'-(4,4'-(1,1':4'1"-terphenyl))diacrylic acid.

$[\alpha]_D^{28} = -17°$ (c=0.05, tetrahydrofuran); NMR (DMSO $d_6$) δ: 3.50(2H,t,J=10 Hz), 3.79–3.93(2H,m), 3.88(6H,s), 4.23–4.33(2H,m), 4.38–4.53(4H,m), 7.29(2H,d,J=16 H) z), 7.72(2H,d,J=16 Hz), 7.83(4H,d,J=8 Hz), 7.88(4H,s), 7.93 (4H,d,J=8 Hz), 8.13(2H,s), 10.56(2H,s), 13.06(2H,s).

In a similar manner, 13.0 mg (50%) of (S,S)-3,3'-[3,3'-(1,4-phenylene)diacryloy]-bis[1-chloromethyl-5-hydroxy-8-methyl-1,2,3,6-tetrahydropyrrolo[3,2-e]indole] was obtained from 27.0 mg (80 μmol) of (S)-3-t-butoxycarbonyl-1-chloromethyl-5-hydroxy-8-methyl-1 2,3,$^6$-tetrahydropyrrolo[3,2-e]indole and 8.7 mg (40 μmol) of 3,3'-(1,4-phenylene)diacrylic acid.

$[\alpha]_D^{28} = -42°$ (c=0.05, tetrahydrofuran); NMR (DMSO $d_6$) δ: 2.35(6H,s), 3.54–3.63(2H,m) , 3.84–3.91(2H,m), 4.00–4.10(2H,m), 4.34–4.54(4H,m), 7.03(2H,s), 7.29(2H,d, j=16 Hz), 7.65(2H,d,J=16 Hz), 7.78(2H,s), 7.86(4H,s), 9.75 (2H,s), 10.68(2H,s).

Example 18

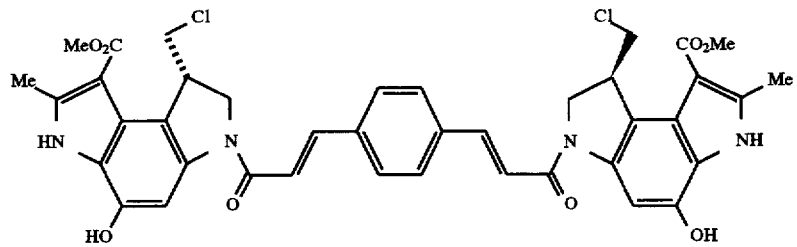

In a similar manner, 8.8 mg (29%) of (S,S)-3,3'-[3,3'-(1,4-phenylene)diacryloyl]-bis[1-chloromethyl-5-hydroxy-7-methyl-1,2,3,6-tetrahydropyrrolo [3,2-e]indole-8-methoxycarbonyl]was obtained from 31.6 mg (80 μmol) of methyl (S)-3-t-butoxycarbonyl-1-chloromethyl-5-hydroxy-7-methyl-1,2,3,6-tetrahydropyrrolo[3,2-e]indole-8-carboxylate and 8.7 mg (40 μmol) of 3,3'-(1,4-phenylene) diacrylic acid.

$[\alpha]_D^{28} = -15°$ (C=0.05, tetrahydrofuran); NMR (DMSO $d_6$) δ: 2.61(6H,s), 3.41–3.47(2H,m), 3.80(6H,s), 3.77–3.90 (2H,m), 4.29–4.50(6H,m), 7.30(2H,d,J=15 Hz), 7.66(2H,d, J=15 Hz), 7.87(4H,s), 7.93(2H,s), 10.11(2H,s), 11.88(2H,s).

Example 19

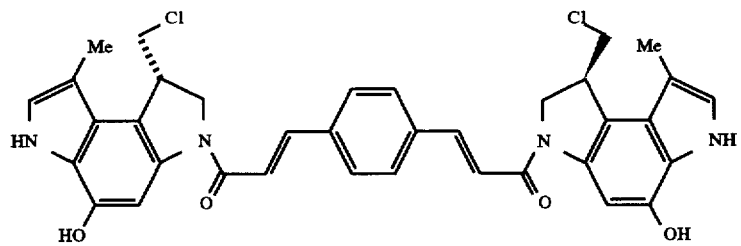

Example 20

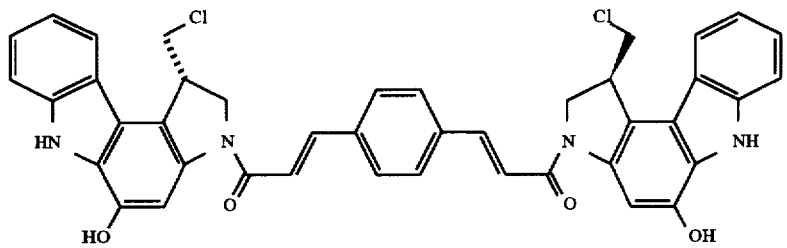

In a similar manner, 1.5 mg (10%) of (S,S)-3,3'-[3,3'-(1,4-phenylene)diacryloyl]-bis[1-chloromethyl-5-hydroxy-1,2-dihydropyrrolo[3,2-a]carbazole] was obtained from 14.9 mg (40 μmol) of (S)-3-t-butoxycarbonyl-1-chloromethyl-5-hydroxy-1,2-dihydropyrrolo[3,2-a] carbazole and 4.4 mg (20 μmol) of 3,3'-(1,4-phenylene)diacrylic acid.

$[\alpha]_D^{28}=-41°$ (c=0.05, tetrahydrofuran); NMR (DMSO $d_6$) δ: 3.83(2H,dd,J=8 and 11Hz), 3.98–4.05(2H,m), 4.34–4.42(2H,m), 4.53–4.64(4H,m), 7.18(2H,t,J=7 Hz), 7.34(2H,d,J=15 Hz), 7.39(2H,t,J=7 Hz), 7.51(2H,d,J=7 Hz), 7.69(2H,d,J=15 Hz), 7.90(4H,s), 7.91(2H,d,J=7 Hz), 8.11(2H,s), 10.08(2H,s), 11.20(2H,s).

Example 21

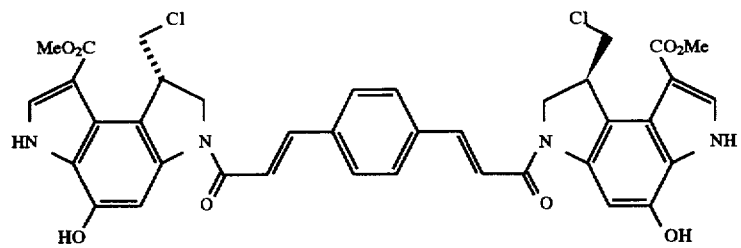

In a similar manner, 2.8 mg (30%) of (S,S)-3,3'-[3,3'-(1,4-phenylene)diacryloyl]-bis[1-chloromethyl-5-hydroxy-1,2,3,6-tetrahydropyrrolo[3,2-e]indole-8-methoxycarbonyl] was obtained from 9.5 mg (25 μmol) of methyl (S)-3-t-butoxycarbonyl-1-chloromethyl-5-hydroxy-1,2,3,6-tetrahydropyrrolo[3,2-e]indole-8-carboxylate and 2.7 mg (12.5 μmol) of 3,3'-(1,4-phenylene)diacrylic acid.

$[\alpha]_D^{26}=-8°$ (c=0.05, tetrahydrofuran); NMR (DMSO $d_6$) δ: 3.45–3.58(2H,m), 3.80(6H,s), 3.72–3.88(2H,m) 3.94(2H,d,J=8.8 Hz), 4.31–4.44(2H,m), 4.48(2H,d,J=8.8 Hz), 7.31 (2H,d,J=15 Hz), 7.67(2H,d,J=15 Hz), 7.88(4H,s), 7.93(2H,d,J=2.9 Hz), 7.97(2H,brs), 10.21(2H,s), 12.03(2H,s).

Example 22

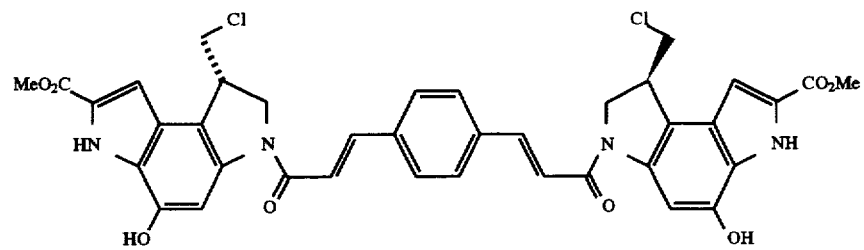

In a similar manner, 2.2 mg (6%) of (S,S)-3,3'-[3,3'-(1,4-phenylene)diacryloyl]-bis[1-chloromethyl-5-hydroxy-1,2,3,6-tetrahydropyrrolo[3,2-e]indole-7-methoxycarbonyl] was obtained from 38.1 mg (100 μmol) of methyl (S)-3-t-butoxycarbonyl-1-chloromethyl-5-hydroxy-1,2,3,6-tetrahydropyrrolo[3,2-e]indole-7-carboxylate and 10.9 mg (50 μmol) of 3,3'-(1,4-phenylene)diacrylic acid.

$[\alpha]_D^{28}=+21°$ (c=0.05, tetrahydrofuran); NMR (DMSO $d_6$) δ: 3.87(6H,s), 3.90–3.99(2H,m), 4.02–4.16(4H,m), 4.28–4.37(2H,m), 4.52–4.63(2H,m), 7.26(2H,d,J=15 Hz), 7.22–7.30(2H,m), 7.66(2H,d,J=15 Hz), 7.85(4H,s), 7.92(2H,s), 9.79(2H,s), 11.61(2H,s).

Reference Example 1

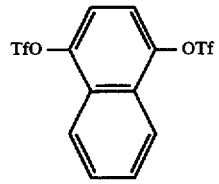

To 100 mg (0.62 mmol) of naphthoquinone, were added 10.0 mg of 10% palladium carbon, and 2 mL of anhydrous tetrahydrofuran. The mixture was stirred under a hydrogen atmosphere at room temperature for 2 hours. Thereto, 0.40 mL (3.03 mmol) of 2,4,6- collidine and 0.26 mg (1.55 mmol) of triflic anhydride were added with ice cooling, and the mixture was stirred under an argon atmosphere at room temperature for 2 hours. The reaction mixture was filtered, and the solvent was removed by distillation. The residue was dissolved in methylene chloride. The solution was washed successively with water, 1N hydrochloric acid, and saturated sodium chloride solution, and was dried over anhydrous sodium sulfate. The solvent was removed by distillation. The product was purified by silica gel column chromatography (hexane:ethyl acetate=10:1) to obtain 78.7 mg (30%) of 1,4-bis (((trifluoromethyl)sulfonyl)oxy)-naphthalene in a state of a colorless oil.

High resolution mass spectrum as $C_{12}H_6F_6O_6S_2$; Calculated: 423.9510 Found: 423.9512

Reference Example 2

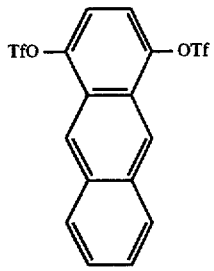

In a similar manner, 450 mg (66%) of 1,4-bis(((trifluoromethyl)sulfonyl)oxy)anthracene was obtained from 300 mg (1.44 mmol) of 1,4-anthraquinone.

Melting point 152.5°–153.5° C.; Elemental analysis as $C_{16}H_8F_6O_6S_2$ Calculated: C, 40.51; H, 1.70; Found: C, 40.31; H, 1.54; Mass spectrum (m/z): 474 (M$^+$)

Reference Example 3

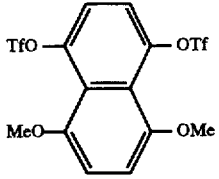

In a similar manner, 163 mg (15%) of 1,4-bis (((trifluoromethyl)sulfonyl) oxy-5,8-dimethoxynaphthalene was obtained from 500 mg (2.29 mmol) of 5,8-dimethoxynaphthoquinone.

Melting point 145.5°–146.5° C.; Elemental analysis as $C_{14}H_{10}F_6O_8S_2$ Calculated: C, 34.72; H, 2.08; Found: C, 34.88; H, 1.82; Mass spectrum (m/z): 484 (M$^+$)

Reference Example 4

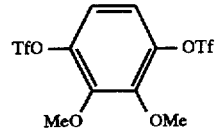

In a similar manner, 218 mg (84%) of 1,4-bis((trifluoromethyl)sulfonyl)oxy)-2,3-dimethoxybenzene was obtained from 100 mg (0.59 mmol) of 2,3-dimethoxybenzoquinone.

High resolution mass spectrum as $C_{10}H_8F_6$ $O_8S_2$ Calculated: 433.9565; Found: 433.9564

Reference Example 5

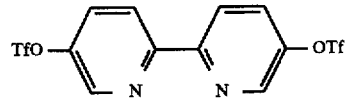

In a similar manner, 567 mg (84%) of 5,5'-bis(((trifluoromethyl)sulfonyl)oxy)-2,2,1-bipyridyl was prepared from 280 mg (1.49 mol) of 5,5'-dihydroxy-2,2'-bipyridyl.

Melting point 158.0°–162.0° C.; Elemental analysis as $C_{12}H_6F_6N_2O_6S_2$ Calculated: C, 31.87; H, 1.34; N, 6.19; Found: C, 31.72; H, 1.14; N, 6.40; Mass spectrum (m/z): 452 (M$^+$)

Reference Example 6

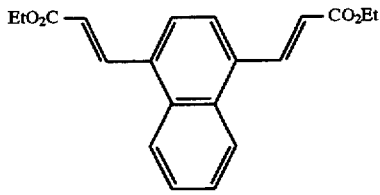

In 5 mL of anhydrous dimethylformamide, were suspended 30.0 mg (71 mol) of 1,4-bis(((trifluoromehyl)-sulf only)oxy)naphthalene, 0.04 mL (0.29 mmol) of triethylamine, 0.16 mL (1.5 mmol) of ethyl acrylate, 2.9 mg (7.0 μmol) of 1,3-diphenylphosphinopropane, and 1.6 mg (7.1 μmol) of palladium acetate. The suspension was stirred overnight under an argon atmosphere at 80° C. Thereto, methylene chloride was added. The mixture was washed successively with 5% hydrochloric acid, water, saturated sodium chloride solution, and dried over anhydrous sodium sulfate. The solvent was removed by distillation. The resulting residue was purified by silica gel column chromatography (methylene chloride:hexane=1:1) to obtain 19.5 mg (85%) of ethyl 3,3'-(1,4-naphthalenediyl)diacrylate in a yellow crystal state.

Melting point 84.0°–87.09° C. Elemental analysis as $C_{20}H_{20}O_4$ Calculated: C, 74.06; H, 6.21; Found: C, 73.89; H, 6.21; Mass spectrum (m/z): 324 (M$^+$)

Reference Example 7

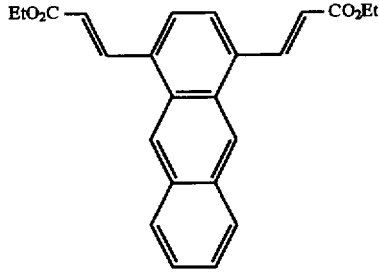

In a similar manner, 169 mg (71%) of ethyl 3,3'-(1,4-anthracenediyl)diacrylate was obtained from 300 mg (0.63 mmol) of 1,4-bis(((trifluoromethyl)sulfonyl)-oxy) anthracene.

Melting point 98.5°–99.5° C. Elemental analysis as $C_{24}H_{22}O_4$ Calculated: C, 76.99; H, 5.92; Found: C, 76.76; H, 6.04; Mass spectrum (m/z): 374 (M$^+$)

Reference Example 8

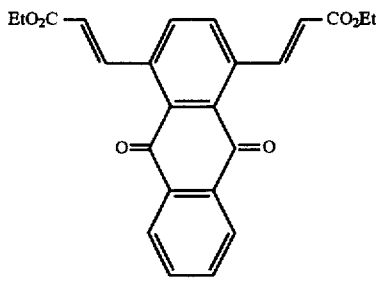

In a similar manner, 49.0 mg (61%) of ethyl 3,3'-(9,10-dihydro-9,10-dioxo-1,4-anthracenediyl)diacrylate was obtained from 100 mg (0.20 mmol) of 1,4-bis(((trifluoromethyl)sulfonyl)oxy) -9,10-dihydro-9,10-dioxoanthracene.

Melting point 222.5°–224.5° C. Elemental analysis as $C_{24}H_{20}O_6$ Calculated: C, 71.28; H, 4.98; Found: C, 71.09; H, 4.93; Mass spectrum (m/z): 404 ($M^+$)

Reference Example 9

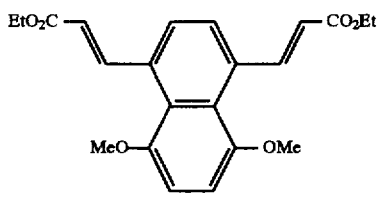

In a similar manner, 219 mg (92%) of ethyl 3,3'-(5,8-dimethoxy-1,4-naphthalenediyl)diacrylate was obtained from 300 mg (0.62 mmol) of 1,4-bis(((trifluoromethyl)sulfony 1)oxy)-5,8-dimethoxynaphthalene.

Melting point 119.0°–122.0° C. Elemental analysis as $C_{22}H_{24}O_6$ Calculated: C, 68.74; H, 6.29; Found: C, 68.50; H, 6.27; Mass spectrum (m/z): 384 ($M^+$)

Reference Example 10

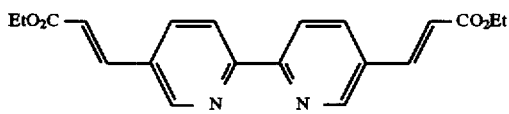

In a similar manner, 54.3 mg (84%) of ethyl 3,3'-(2,2-bipyridyl-5,5'-diyl)diacrylate was obtained from 83.2 mg (0.18 mmol) of 5,5'-1,4-bis(((trifluoromethyl)sulfonyl)-ox y)-2,2'-bipyridyl.

Melting point 173.5°–175.0° C. Elemental analysis as $C_{20}H_{20}N_2O_4$ Calculated: C, 68.17; H, 5.72; N, 7.95; Found: C, 67.89; H, 5.64; N, 7.93; Mass spectrum (m/z): 352 ($M^+$)

Reference Example 11

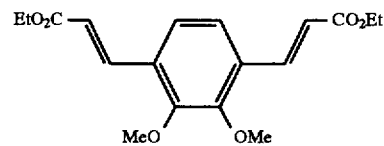

In 2.3 mL of anhydrous dimethylformamide, were suspended 200 mg (0.46 mmol) of 1,4-bis(((trifluoromethyl)-su lfonyl)oxy)-2,3-dimethoxybenzene, and 58.5 mg (1.38 mmol) of lithium chloride. Gaseous argon was blown therein to remove air. Further thereto, 16.1 mg (23 µmol) of bis (triphenylphosphine)palladium dichloride was added. The mixture was stirred at 100° C. for 30 minutes. Thereto, a solution of 537 mg (1.38 mmol) of ethyl 3-(tributylstannyl) acrylate in 0.5 mL of anhydrous dimethylformamide was added. The mixture was stirred at 100° C. for 30 minutes. Methylene chloride was added thereto, and the mixture was washed successively with water, and 5% potassium fluoride, and dried over anhydrous sodium sulfate. The solvent was removed by distillation. The resulting residue was purified by silica gel column chromatography (ethyl acetate:hexane= 1:6) to obtain 18.6 mg (14%) of ethyl 3,3'-(2,3-dimethoxy-1,4-phenylene)diacrylate in a colorless prism crystal state.

Melting point 88.5°–89.5° C. Elemental analysis as $C_{18}H_{22}O_6$ Calculated: C, 64.66; H, 6.63; Found: C, 64.45; H, 6.66; Mass spectrum (m/z): 334 ($M^+$)

Reference Example 12

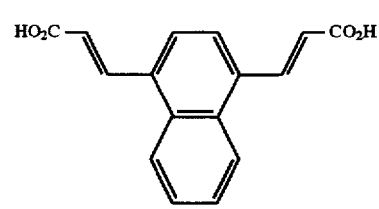

In 2 mL of ethanol, were dissolved 115 mg (0.35 mmol) of ethyl 3,3'-(1,4-naphthalenediyl)diacrylate and 196 mg (3.49 mmol) of potassium hydroxide. The solution was refluxed for 2 hours. Thereto, 1N hydrochloric acid was added to bring the solution to pH=1. The deposited crystal was washed successively with water, and ethanol, and dried to obtain 90.2 mg (95%) of 3,3'-(1,4-naphthalenediyl)-diacrylic acid in a yellow crystal state.

Melting point 350.0°–355.0° C. High resolution mass spectrum as $C_{16}H_{12}O_4$; Calculated: 268.0736; Found: 268.0743

Reference Example 13

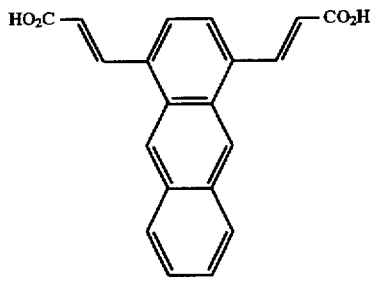

In a similar manner, 152 mg (89%) of 3,3'-(1,4-anthracenediyl)diacrylic acid was obtained from 200 mg (0.53 mmol) of ethyl 3,3'-(1,4-anthracenediyl)diacrylate.

Melting point 328.5°–338.0° C. (decomposed) High resolution mass spectrum as $C_{20}H_{14}O_4$; Calculated: 318.0892; Found: 318.0894

Reference Example 14

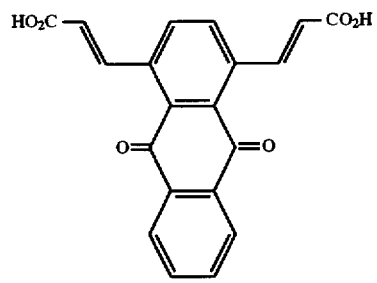

In a similar manner, 215 mg (100%) of 3,3'-(9,10-dihydro-9,10-dioxo-1,4-anthracenediyl)diacrylic acid was obtained from 250 mg (0.62 mmol) of ethyl 3,3'-(9,10-dihydro-9,10-dioxo-1,4-anthracenediyl)diacrylate.

Melting point 323.0°–338.0° C. (decomposed) Elemental analysis as $C_{20}H_{12}O_6$; Calculated: C, 68.97; H, 3.47; Found: C, 68.71; H, 3.31

Reference Example 15

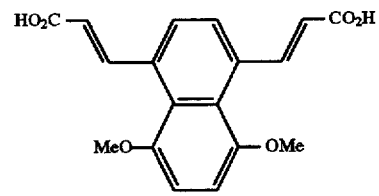

In a similar manner, 79.5 mg (93%) of 3,3'-(5,8-dimethoxy-1,4-naphthalenediyl)diacrylic acid was obtained from 100 mg (0.26 mmol) of ethyl 3,31-(5,8-dimethoxy-1,4-naph thalenediyl)diacrylate.

Melting point 290.0°–299.5° C. (decomposed) High resolution mass spectrum as $C_{18}H_{15}O_6$; Calculated: 327.0869; Found: 327.0934

Reference Example 16

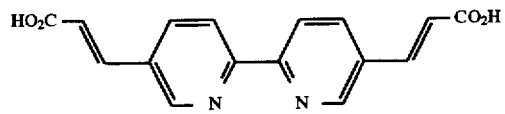

In a similar manner, 73.8 mg (88%) of 3,3'-(2,2'-bipyridyl-5,5'-diyl)diacrylic acid was obtained from 100 mg (0.28 mmol) of ethyl 3,3'-(2,2'-bipyridyl-5,5'-diyl)diacrylate.

Melting point 447.0°–454.0° C. (decomposed) High resolution mass spectrum as $C_{16}H_{12}N_2O_4$; Calculated: 297.0875; Found: 297.0875

Reference Example 17

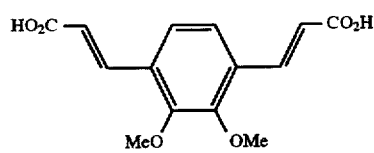

In a similar manner, 36.3 mg (98%) of 3,3'-(2,3-dimethoxy-1,4-phenylene)diacrylic acid was obtained from 44.5 mg (0.13 mmol) of ethyl 3,3'-(2,3-dimethoxy-1,4-phenylene)dia crylate.

Melting point 304.0°–315.5° C. (decomposed) High resolution mass spectrum as $C_{14}H_{14}O_6$; Calculated: 278.0790; Found: 278.0802

Reference Example 18

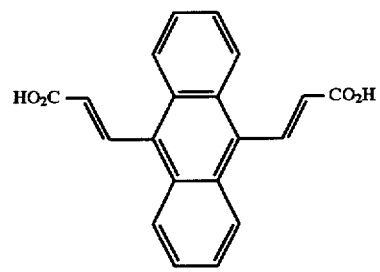

In a similar manner, 161 mg (96%) of 3,3'-(9,10-anthracenediyl)diacrylic acid was obtained from 200 mg (0.53 mmol) of ethyl 3,3'-(9,10-anthracenediyl)diacrylate.

Melting point 310.5°–319.0° C. (decomposed) High resolution mass spectrum as $C_{20}H_{14}O_4$; Calculated: 318.0892; Found: 318.0915

Reference Example 19

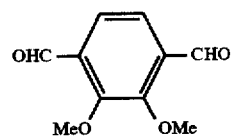

To 13.6 g (47.1 mmol) of sodium bis(2-methoxyethoxy) aluminum hydride (70% toluene solution), was added a solution of 5.20 g (51.9 mmol) of N-methylpiperazine in 23 mL of anhydrous toluene to prepare a reagent. Separately, 3.00 g (11.8 mmol) of methyl 2,3-dimethoxy-1,4-benzenedicarboxylate was dissolved in 120 mL of anhydrous toluene. To this solution, the above reagent was added at a temperature of from −20° to −17° C., and the mixture was stirred for 10 minutes. Water was added to the reaction mixture, and the insoluble matter was removed therefrom. The solution was washed successively with 1N hydrochloric acid, water, saturated sodium chloride solution, and was dried over anhydrous sodium sulfate. The solvent was removed by distillation, and the product was purified by silica gel chromatography (methylene chloride) to obtain 1.84 g (80%) of 2,3-methoxy-1,4-benzenedicarbaldehyde in a colorless crystal state.

Melting point 99.5°–100.5° C. Elemental analysis as $C_{10}H_{10}O_4$ Calculated: C, 61.85; H, 5.19; Found: C, 61.74; H, 5.18; Mass spectrum (m/z) : 194 ($M^+$)

Reference Example 20

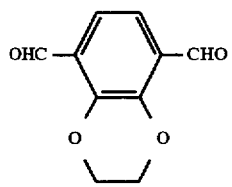

In a similar manner, 371 mg (16%) of 2,3-(ethylenedioxy)-1,4-benzenedicarbaldehyde was obtained from 3.00 a (11.9 mmol) of methyl 2,3-(ethylenedioxy)-1,4-benzenedicarboxylate.

Melting point 139.0°–140.5° C. Elemental analysis as $C_{10}H_8O_4$ Calculated: C, 62.50; H, 4.20 Found: C, 62.47; H, 4.26 Mass spectrum (m/z): 192 ($M^+$)

Reference Example 21

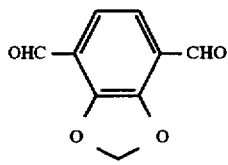

In a similar manner, 1.52 g (68%) of 2,3-(methylenedioxy)-1,4-benzenedicarbaldehyde was obtained from 3.00 g (12.6 mmol) of methyl 2,3-(methylenedioxy)-1,4-benzenedicarboxylate.

Melting point 151.5°–152.0° C. Elemental analysis as $C_9H_6O_4$ Calculated: C, 60.68; H., 3.39; Found: C, 60.59; H, 3.40; Mass spectrum (m/z): 178 ($M^+$)

Reference Example 22

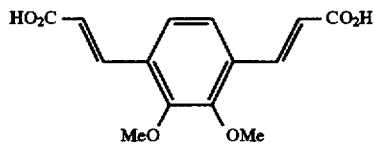

A liquid suspension composed of 1.00 (5.15 mmol) of 2,3-dimethoxy-1,4-benzenedicarbaldehyde, 2.37 g (22.8 mmol) of malonic acid, 0.1 mL of piperidine, and 7.0 mL of pyridine was refluxed for 16 hours. The reaction mixture was cooled with ice, and the pH was adjusted to 2 by addition of 1N hydrochloric acid. The deposited crystalline matter was collected by filtration, and was washed successively with water, ethanol, and methylene chloride to obtain 1.34 g (94%) of 3,3'-(2,3-dimethoxy-1,4-phenylene)diacrylic acid.

Reference Example 23

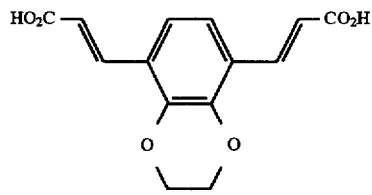

In a similar manner, 1.39 g (96%) of 3,3'-(2,3-(ethylenedioxy)-1,4-phenylene)diacrylic acid was obtained from 1.01 g (5.26 mmol) of 2,3-(ethylenedioxy)-1,4-benzenedicarbaldehyde.

Melting point 344.5°–348.5° C. High resolution mass spectrum as $C_{14}H_{12}O_6$; Calculated: 276.0634; Found: 276.0634

Reference Example 24

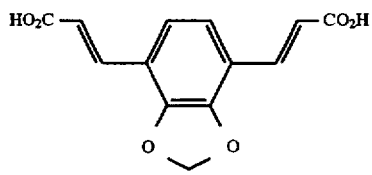

In a similar manner, 1.39 g (94%) of 3,3'-(2,3-(methylenedioxy)-1,4-phenylene)diacrylic acid was obtained from 1.00 g (5.61 mmol) of 2,3-(methylenedioxy)-1,4-benzenedicarbaldehyde.

Melting point 334.0°–338.0° C. High resolution mass spectrum as $C_{13}H_{10}O_6$; Calculated: 262.0477; Found: 262.0462

Reference Example 25

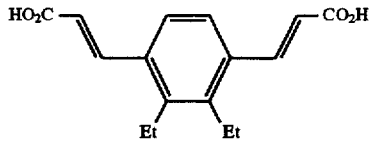

In a similar manner, 62.6 mg (74%) of 3,3'-(2,3-diethyl-1,4-phenylene)diacrylic acid was obtained from 59.8 mg (0.31 mmol) of 2,3-diethyl-1,4-benzenedicarbaldehyde.

Melting point 264.0°–268.0° C. (decomposed) High resolution mass spectrum as $C_{16}H_{18}O_4$; Calculated: 274.1205; Found: 274.1160

Reference Example 26

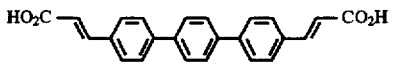

In a similar manner, 96.4 mg (93%) of 3,3'-(4,4"-(1,1':4", 4"-terphenyl))diacrylic acid was obtained from 80 mg (0.28 mmol) of (1,1':4'4"-terphenyl))-4,4"-dicarbaldehyde.

Melting point 340.0°–345.0° C. Elemental analysis as $C_{24}H_{18}O_4$; Calculated: C, 77.82; H, 4.39; Found: C, 77.72; H, 5.10

Reference Example 27

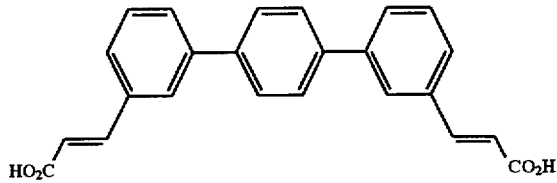

In a similar manner, 1.06 g (95%) of 3,3'-(3,3"-(1,1':4', 4"-terphenyl))diacrylic acid was obtained from 859 mg (3.00 mmol) of (1,1':4', 4"-terphenyl)-3,3"-dicarboxyaldehyde.

Melting point 337.0°–343.0° C. High resolution mass spectrum as $C_{24}H_{17}O_4$; Calculated: 369.1127; Found: 369.1214

Reference Example 28

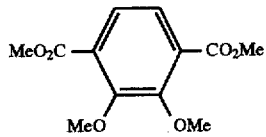

In 50 mL of anhydrous dimethylformamide, 5.00 g (22.1 mmol) of methyl 2,3-dihydroxy-1,4-benzenedicarboxylate was dissolved. Thereto, 17.3 g (53.1 mmol) of cesium carbonate was added. The solution was stirred under an argon atmosphere at room temperature for 30 minutes. Further thereto, 3.31 mL (53.2 mmol) of methyl iodide was added, and the mixture was stirred at room temperature for 2 hours. The reaction solution was concentrated at a reduced pressure. Methylene chloride was added thereto. The mixture was washed successively with water, and a saturated sodium chloride solution, and was dried over anhydrous sodium sulfate. The solvent was removed therefrom by distillation to obtain 5.55 g (99%) of methyl 2,3-dimethoxy-1,4-benzenedicarboxylate. Mass spectrum (m/z) : 254 ($M^+$)

Reference Example 29

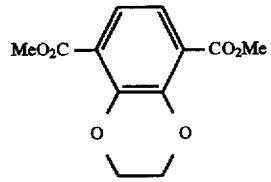

In a similar manner, 5.54 g (99%) of methyl 2,3-(ethylenedioxy)-1,4-benzenedicarboxylate was obtained from 5.00 g (22.1 mmol) of methyl 2,3-dihydroxy-1,4-benzenedicarboxylate.

Melting point 107.5°–110.0° C.; Mass spectrum (m/z): 252 ($M^+$)

Reference Example 30

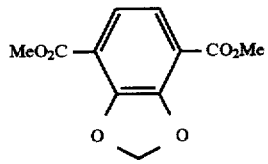

In a similar manner, 5.14 g (98%) of methyl 2,3-(methylenedioxy)-1,4-benzenedicarboxylate was obtained from 5.00 g (22.1 mmol) of methyl 2,3-dihydroxy-1,4-benzenedicarboxylate.

Melting point 208.0°–210.0° C.; Mass spectrum (m/z): 238 ($M^+$)

Reference Example 31

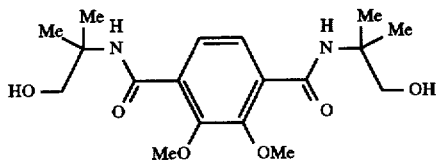

In 8 mL of anhydrous methylene chloride, was dissolved 6.06 g (68.0 mmol) of 2-amino-2-methyl-1-propanol. Thereto, a solution of 4.47 g (17.0 mmol) of 2,3-dimethoxy-1,4-benzenedicarboxylic chloride in 8 mL of anhydrous methylene chloride was added by keeping the inner temperature at 5°–10° C., and the mixture was stirred at room temperature for 2 hours. The reaction mixture was filtered, and washed with water. The filtrate and the wash water were combined and concentrated under a reduced pressure. Methylene chloride was added to the obtained residue, and the mixture was dried over anhydrous sodium sulfate. The solvent was removed. The product was recrystallized from benzene to obtain 6.27 g (100%) of N,N'-bis(2-hydroxy-1,1-dimethylethyl)-2,3-dimethoxy-1,4-phenylenedicarboxamide in a colorless prism crystal state.

Melting point 151.0°–153.0° C. Elemental analysis as $C_{18}H_{28}N_2O_6$ Calculated: C, 58.68; H, 7.66; N, 7.60; Found: C, 58.65; H, 7.79; N, 7.44; Mass spectrum (m/z): 368 ($M^+$)

Reference Example 32

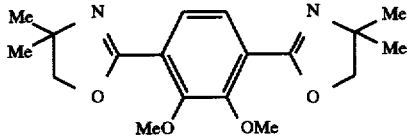

To 6.00 g (16.3-mmol) of N,N'-bis(2-hydroxy-1,1-dimethylethyl)-2,3-dimethoxy-1,4-phenylenedicarboxamide, was added 7.0 mL (96.0 mmol) of thionyl chloride. The mixture was stirred at room temperature for 3 hours. Further thereto, 7.0 mL (96.0 mmol) of thionyl chloride was added, and the mixture was stirred at room temperature for one hour. The reaction solution was poured into 50 mL of ether. The supernatant liquid was removed by decantation. Aqueous 10% sodium hydroxide solution was added to the residue to bring the pH to 8. It was extracted with ether, and was dried over anhydrous sodium sulfate. The solvent was removed by distillation, and the residue was purified by silca gel column chromatography (methylene chloride:ethanol=20:1) to obtain 2.52 g (47%) of 2,2'-(2,3-dimethoxy-1,4-phenylene)-bis (4,4-dimethyl-2-oxazoline) in a colorless crystal state.

Melting point 84.5°–85.5° C. Elemental analysis as $C_{18}H_{24}N_2O_4$ Calculated: C, 65.04; H, 7.28; N, 8.43; Found: C, 64.96; H, 7.16; N, 8.41; Mass spectrum (m/z): 332 (M⁺)

Reference Example 33

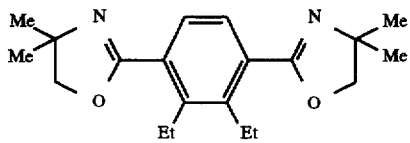

In 20 mL of anhydrous tetrahydrofuran, was dissolved 2.00 g (6.02 mmol) of 2,2'-(2,3-dimethoxy-1,4-phenylene)-bis(4,4-dimethyl-2-oxazoline). Thereto, 16.4 mL of 0.92M ethylmagnesium bromide solution (15.1 mmol) in tetrahydrofuran was added dropwise with ice cooling in 30 minutes, and the mixture was stirred at room temperature for 2 hours. To the reaction liquid, were added successively 10 mL of aqueous saturated ammonium chloride solution and 30 mL of water. The product was extracted from the mixture with ether, washed with a saturated sodium chloride solution, and dried over anhydrous sodium sulfate. The solvent was removed by distillation. The residue was purified by silica gel column chromatography (ethyl acetate:hexane=2:1) to obtain 1.98 g (100%) of 2,2'-(2,3-diethyl-1,4-phenylene)-bis (4,4-dimethyl-2-oxazoline) in a colorless prism crystal state.

Melting point 49.0°–50.0° C. Elemental analysis as $C_{20}H_{28}N_2O_2$; Calculated: C, 73.14; H, 8.59; N, 8.53; Found: C, 72.97; H, 8.56; N, 8.46 Mass spectrum (m/z): 328 (M⁺)

Reference Example 34

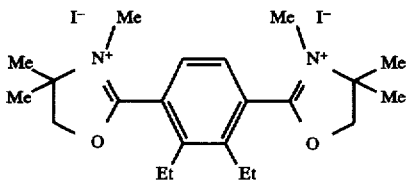

To 1.86 g (5.66 mmol) of 2,2'-(2,3-diethyl-1,4-phenylene)-bis(4,4-dimethyl-2-oxazoline), were added 5.0 mL of nitromethane and 7.0 mL (122 mmol) of methyl iodide. The mixture was stirred at 80° C. for 4 hours. The reaction liquid was poured into 30 mL of ether. The deposited crystalline matter was collected by filtration, and was recrystallized from ethanol to obtain 2.62 g (76%) of 2,2'-(2,3-diethyl-1,4-phenylene)-bis(3,4,4-trimethyl-2-oxazolium iodide).

Melting point 281.0°–285.0° C. Elemental analysis as $C_{22}H_{34}I_2N_2O_2$ Calculated: C, 43.15; H, 5.60; N, 4.57; Found: C, 43.05; H, 5.41; N, 4.72; Mass spectrum (m/z) : 329 (M⁺+1–2MeI)

Reference Example 35

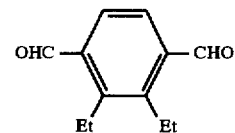

In 50 mL of ethanol, was suspended 2.45 g (4.00 mmol) of 2,2'-(2,3-diethyl-1,4-phenylene)-bis(3,4,4-trimethyl 1-2-oxazolium iodide). Thereto, 770 mg (20.4 mmol) of sodium boron hydride was added dropwise with ice cooling in one hour, and the mixture was stirred at 5° C. for 3 hours. Hydrochloric acid (2N) was added to the reaction liquid. The product was extracted with ether from the reaction liquid, washed with an aqueous saturated sodium chloride solution, and dried over anhydrous sodium sulfate. Active carbon was added to the solution. The solution was filtered, and the solvent was removed by distillation to obtain 102 mg (13%) of 2,3-diethyl-1,4-benzenecarbaldehyde in a colorless prism crystal state.

Melting point 32.0°–34.5° C. High resolution mass spectrum as $C_{12}H_{14}O_2$; Calculated: 190.0994; Found: 190.0990

Experimental Example 1

HeLa Cell Growth Inhibition Activity:

HeLa $S_3$ cells were maintained as a monolayer culture in Eagle's minimal medium (Nissui Seiyaku K. K., Tokyo) containing 2 m glutamine, 100 µg/mL of kanamycin sulfate, and 10% inactivated fetal calt serum at 37° C. in a carbon dioxide incubator. The cells $1.8 \times 10^3$ were inoculated to a 96-well plate, and were exposed to the test compounds from the next day for 72 hours. Then, the viable cell numbers were measured by evaluating the ability to reduce 3-[4,5-dimethylthiazol-2-yl]-2,5-diphenyltetrazolium bromide (MTT) according to the Mosmann's method (Mosmann,T., J. Imunol. Meth., 65, 55–63, 1983). Table 1 shows the cell growth inhibition activities as a 50% inhibition concentration which is calculated from the dependence of the ratio of growth of the compound-treated cells to the growth of non-treated cells on the compound concentration.

Experimental Example 2

Antitumor effect in Colon 26-bearing mice:

Colon 26 cells $1 \times 10^6$ were transplanted into an axillary region of 8-week old $CDF_1$ female mice (Japan SLC Inc., Hamamatsu) subcutaneously. Six days after the transplantation, when the tumor grew palpable, the compound was administered via the tail vein. One week after the administration, the tumor was removed and weighed. The antitumor activity was represented by tumor growth inhibition rate (TGI %=(1—T/C)×100) derived from the ratio (T/C) of the average tumor weight (T) of the compound-administered group to the average tumor weight (C) of the control group. Table 1 shows the tumor growth inhibition rate.

Table 1 shows also the chemotherapy index ($MTD/TGI_{50}$) defined by the ratio of the maximum tolerant dose for the mice (MTD, mg/kg) to the dose ($TGI_{50}$, mg/kg) at which the tumor growth inhibition rate (TGI) is 50% in colon26-bearing mice.

TABLE 1

| Example No. | Cell growth inhibition HeLa S₃ IC$_{50}$ (ng/mL) | Antitumor activity Colon-26 TGI % (μg/kg) | Chemotherapy index MTD/TGI$_{50}$ |
|---|---|---|---|
| 1 | 0.0031 | 92 (7.81) | 21.9 |
| 3 | 0.00934 | — | — |
| 4 | 0.00276 | 91 (0.488) | 9 |
| 5 | 0.00595 | 90 (1.95) | — |
| 6 | 0.0318 | — | — |
| 8 | 0.00158 | 89 (0.977) | 4.6 |
| 10 | 0.011 | 85 (0.977) | 7.4 |
| 13 | 0.0198 | 88 (3.91) | 3.6 |
| 18 | 0.000459 | — | — |
| 19 | 0.0134 | — | — |
| 20 | 0.0716 | — | — |
| 21 | 0.00035 | — | — |
| 22 | 0.0227 | — | — |

As shown above, the compounds of the present invention exhibited excellent antitumor activity.

Industrial Applicability

The compounds of the present invention have excellent antimicrobial activity and antitumor activity, and yet exhibit high selectivity to cancer cells, and are less toxic. The compounds of the present invention have high cell-killing activity, and antitumor activity over a wide safe region. Therefore, the compounds are effective to tumors having lowered susceptibility to antitumor medicines, and is promising to mitigate the burden of chemotherapy on cancer patients.

What is claimed is:

1. Acrylamide derivatives represented by General Formula (1):

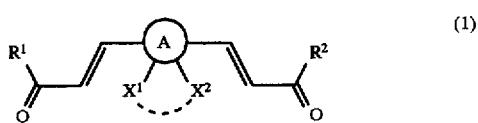

(1)

(wherein $X^1$ and $X^2$ are independently a hydrogen atom, a halogen atom, an amino group, an alkylamino group, an aminoalkyl group, a hydroxyl group, $OR^3$ ($R^3$ being a linear or branched lower alkyl of C1–C6, or a substituted or unsubstituted aryl) $OCOR^3$ ($R^3$ being the same as above), or a linear or branched lower alkyl of C1–C6, and $X^1$ and $X^2$ may be linked together; the ring A is a biphenyl ring, a naphthalene ring, an anthracene ring, or an anthraquinone ring; and $R^1$ and $R^2$ are independently:

a.

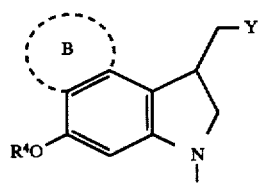

($R^4$ is a hydrogen atom, a protecting group for hydroxyl, or a substituent decomposable in vivo; Y is a halogen atom, an arylsulfonyloxy group, a lower alkylsulfonyloxy group, a haloalkylsulfonyloxy group, or an azide group;

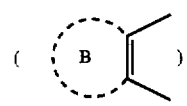

is a condensed ring, or

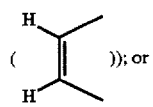

)); or b.

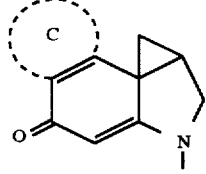

is a condensed ring or

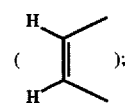

or an optical isomer thereof, or a pharmaceutically acceptable salt thereof.

2. A process for producing a compound of General Formula (3):

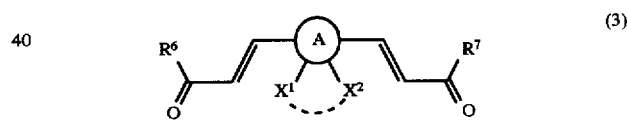

(3)

wherein $X^1$ and $X^2$ are independently a hydrogen atom, a halogen atom, an amino group, an alkylamino group, an aminoalkyl group, a hydroxyl group, $OR^3$ ($R^3$ being a linear or branched lower alkyl of C1–C6, or a substituted or unsubstituted aryl), $OCOR^3$ ($R^3$ being the same as above), or a linear or branched lower alkyl of C1–C6, and $X^1$ and $X^2$ may be linked together; the ring A is a biphenyl ring, a naphthalene ring, an anthracene ring, or an anthraquinone ring; $R^6$ and $R^7$ are independently

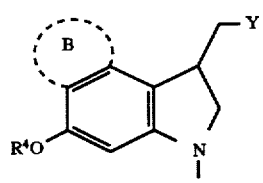

($R^4$ being a hydrogen atom, a protecting group for hydroxyl or a substituent decomposable in vivo; Y being a halogen atom, an arylsulfonyloxy group, a lower alkylsulfonyloxy group, a haloalkylsulfonyloxy group, or an azide group;

((

being a condensed ring, or

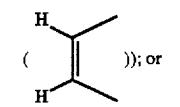

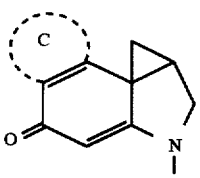

being a condensed ring, or

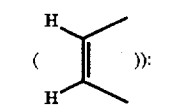

the process comprising acylating a compound of General Formula, or a salt thereof:

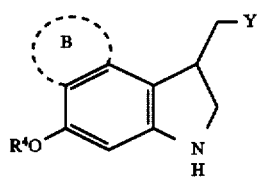

where $R^4$, Y, and

are as defined above, or

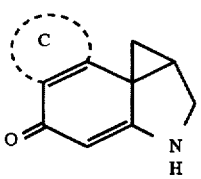

where

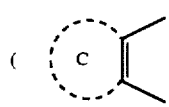

is as defined above, with dicarboxylic acid derivatives represented by General Formula (2):

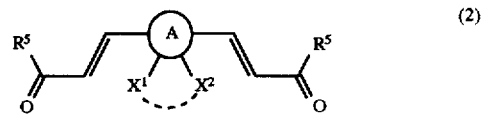

(2)

where $X^1$, $X^2$, and the ring A are as defined above, and $R^5$ is OH or a reactive residue.

3. Acrylamide derivatives, an optically active isomar, or a pharmaceutically acceptable salt thereof as set forth in claim 1, wherein

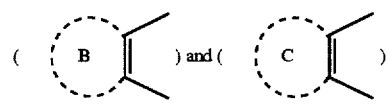

are represented by any of the formulas below:

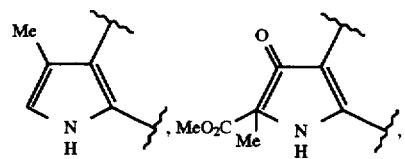

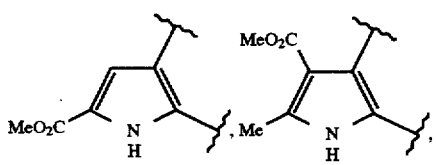

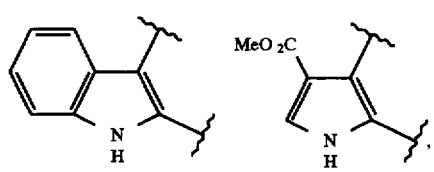

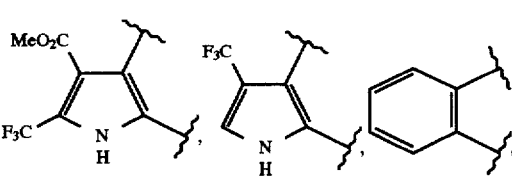

and

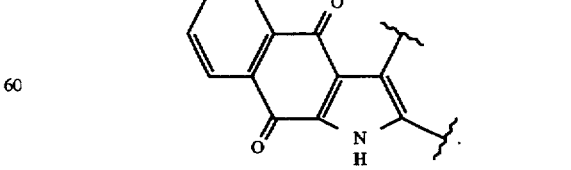

4. A method for treating a patient with a microbial disease comprising: administering to the patient an antimicrobial effective amount of the acrylamide derivative of claim 1.

5. A method for treating a patient with a microbial disease comprising: administering to the patient an antimicrobial effective amount of the acrylamide derivative of claim 3.

6. A method for treating a patient with cancer comprising administering to the patient an anti-tumor effective amount of the acrylamide derivative of claim 1.

7. A method for treating a patient with cancer comprising administering to the patient an anti-tumor effective amount of the acrylamide derivative of claim 3.

8. The method of claim 4, wherein the route of administration of the acrylamide derivative is selected from the group consisting of oral, intravenous, intraarterial, intraperitoneal, hypodermic, intramuscular, intrathoracic and topical.

9. The method of claim 4, wherein the effective amount is from about 0.00001 to about 100 mg of acrylamide derivative per kg of patient per day.

10. The method of claim 4, wherein the frequency of administration of is selected from the group consisting of several times a day, once per day, one to five times a week and at intervals of two to four weeks.

11. The method of claim 5, wherein the route of administration of the acrylamide derivative is selected from the group consisting of oral, intravenous, intraarterial, intraperitoneal, hypodermic, intramuscular, intrathoracic and topical.

12. The method of claim 5, wherein the effective amount is from about 0.00001 to about 100 mg of acrylamide derivative per kg of patient per day.

13. The method of claim 5, wherein the frequency of administration of is selected from the group consisting of several times a day, once per day, one to five times a week and at intervals of two to four weeks.

14. The method of claim 6, wherein the route of administration of the acrylamide derivative is selected from the group consisting of oral, intravenous, intraarterial, intraperitoneal, hypodermic, intramuscular, intrathoracic and topical.

15. The method of claim 6, wherein the effective amount is from about 0.00001 to about 100 mg of acrylamide derivative per kg of patient per day.

16. The method of claim 6, wherein the frequency of administration of is selected from the group consisting of several times a day, once per day, one to five times a week and at intervals of two to four weeks.

17. The method of claim 7, wherein the route of administration of the acrylamide derivative is selected from the group consisting of oral, intravenous, intraarterial, intraperitoneal, hypodermic, intramuscular, intrathoracic and topical.

18. The method of claim 7, wherein the effective amount is from about 0.00001 to about 100 mg of acrylamide derivative per kg of patient per day.

19. The method of claim 7, wherein the frequency of administration of is selected from the group consisting of several times a day, once per day, one to five times a week and at intervals of two to four weeks.

20. The acrylamide derivative of claim 3, wherein the acrylamide derivative is selected from the group consisting of (S,S)-3,3'-[3,3'-(1,4-phenylenediacryloyl)]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(ethylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(methylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(dimethoxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-naphthalenediyl)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-phenylene)diacryloyl]-bis[1-chloromethyl-5-hydroxy-7-methyl-1,2,3,6-tetrahydropyrrolo[3,2-e]indole-8-methoxycarbonyl]; (S,S)-3,3'-[3,3'-(1,4-phenylene)diacryloyl]-bis[1-chloromethyl-5-hydroxy-8-methyl-1,2,3,6-tetrahydropyrrolo[3,2-e]indole]; (S,S)-3,3'-[3,3'-(1,4-phenylene)diacryloyl]-bis[1-chloromethyl-5-hydroxy-1,2-dihydropyrrolo[3,2-a]carbazole]; (S,S)-3,3'-[3,3'-(1,4-phenylene)diacryloyl]-bis[1-chloromethyl-5-hydroxy-1,2,3,6-tetrahydropyrrolo[3,2-e]indole-8-methoxycarbonyl]; and (S,S)-3,3'-[3,3'-(1,4-phenylene)diacryloyl]-bis[1-chloromethyl-5-hydroxy-1,2,3,6-tetrahydropyrrolo[3,2-e]indole-7-methoxycarbonyl].

21. The method of claim 5, wherein the acrylamide derivative is selected from the group consisting of (S,S)-3,3'-[3,3'-(1,4-phenylenediacryloyl)]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(ethylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(methylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(dimethoxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-naphthalenediyl)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-phenylene)diacryloyl]-bis[1-chloromethyl-5-hydroxy-7-methyl-1,2,3,6-tetrahydropyrrolo[3,2-e]indole-8-methoxycarbonyl]; (S,S)-3,3'-[3,3'-(1,4-phenylene)diacryloyl]-bis[1-chloromethyl-5-hydroxy-8-methyl-1,2,3,6-tetrahydropyrrolo[3,2-e]indole]; (S,S)-3,3'-[3,3'-(1,4-phenylene)diacryloyl]-bis[1-chloromethyl-5-hydroxy-1,2-dihydropyrrolo[3,2-a]carbazole]; (S,S)-3,3'-[3,3'-(1,4-phenylene)diacryloyl]-bis[1-chloromethyl-5-hydroxy-1,2,3,6-tetrahydropyrrolo[3,2-e]indole-8-methoxycarbonyl]; and (S,S)-3,3'-[3,3'-(1,4-phenylene)diacryloyl]-bis[1-chloromethyl-5-hydroxy-1,2,3,6-tetrahydropyrrolo[3,2-e]indole-7-methoxycarbonyl].

22. The method of claim 7, wherein the acrylamide derivative is selected from the group consisting of (S,S)-3,3'-[3,3'-(1,4-phenylenediacryloyl)]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(ethylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(methylenedioxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(2,3-(dimethoxy)-1,4-phenylene)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-naphthalenediyl)diacryloyl]-bis[1-chloromethyl-5-hydroxy-7-trifluoromethyl-1,2,3,6-tetrahydropyrrolo[3,2-e]indole-8-methoxycarbonyl]; (S,S)-3,3'-[3,3'-(1,4-phenylene)diacryloyl]-bis[1-chloromethyl-5-hydroxy-7-methyl-1,2,3,6-tetrahydropyrrolo[3,2-e]indole- 8-methoxycarbonyl]; (S,S)-3,3'-[3,3'-(1,4-phenylene)
diacryloyl]-bis[1-chloromethyl-5-hydroxy-8-methyl-1,2,3,
6-tetrahydropyrrolo[3,2-e]indole]; (S,S)-3,3'-[3,3'-(1,4-
phenylene)diacryloyl]-bis[1-chloromethyl-5-hydroxy-1,2-
dihydropyrrolo[3,2-a]carbazole]; (S,S)-3,3'-[3,3'-(1,4-
phenylene)diacryloyl]-bis[1-chloromethyl-5-hydroxy-1,2,3,
6-tetrahydropyrrolo[3,2-e]indole-8-methoxycarbonyl]; and
(S,S)-3,3'-[3,3'-(1,4-phenylene)diacryloyl]-bis[1-
chloromethyl-5-hydroxy-1,2,3,6-tetrahydropyrrolo[3,2-e]
indole-7-methoxycarbonyl].

23. An antimicrobial composition comprising a pharmaceutically acceptable carrier and the acrylamide derivative of claim 1.

24. An antimicrobial composition comprising a pharmaceutically acceptable carrier and the acrylamide derivative of claim 3.

25. An antimicrobial composition comprising a pharmaceutically acceptable carrier and the acrylamide derivative of claim 20.

26. An anti-tumor composition comprising a pharmaceutically acceptable carrier and the acrylamide derivative of claim 1.

27. An anti-tumor composition comprising a pharmaceutically acceptable carrier and the acrylamide derivative of claim 3.

28. An anti-tumor composition comprising a pharmaceutically acceptable carrier and the acrylamide derivative of claim 20.

* * * * *